US012690848B2

(12) United States Patent
Shipp

(10) Patent No.: US 12,690,848 B2
(45) Date of Patent: Jul. 28, 2026

(54) VESSEL SEALING DEVICE

(71) Applicant: Cyndrx, LLC, Brentwood, TN (US)

(72) Inventor: John I. Shipp, Jacksonville, FL (US)

(73) Assignee: CyndRx LLC, Brentwood, TN (US)

(*) Notice: Subject to any disclaimer, the term of this patent is extended or adjusted under 35 U.S.C. 154(b) by 116 days.

(21) Appl. No.: 17/677,622

(22) Filed: Feb. 22, 2022

(65) Prior Publication Data

US 2022/0167956 A1     Jun. 2, 2022

Related U.S. Application Data

(63) Continuation of application No. 16/429,969, filed on Jun. 3, 2019, now Pat. No. 11,253,242, which is a continuation of application No. 14/861,485, filed on Sep. 22, 2015, now Pat. No. 10,307,145, which is a continuation-in-part of application No. 13/746,278, filed on Jan. 21, 2013, now Pat. No. 9,138,215.

(51) Int. Cl.
*A61B 17/00*     (2006.01)
*A61B 90/00*     (2016.01)

(52) U.S. Cl.
CPC ...... *A61B 17/0057* (2013.01); *A61B 2017/00004* (2013.01); *A61B 2017/00659* (2013.01); *A61B 2090/037* (2016.02); *A61B 2090/038* (2016.02); *A61B 2090/0807* (2016.02)

(58) Field of Classification Search
CPC ...... A61B 17/0057; A61B 2017/00654; A61B 2017/00601; A61B 2017/00615; A61B 2017/00623
See application file for complete search history.

(56) References Cited

U.S. PATENT DOCUMENTS

| | | | |
|---|---|---|---|
| 5,342,393 A | 8/1994 | Stack | |
| 5,350,399 A | 9/1994 | Erlebacher et al. | |
| 5,620,461 A | 4/1997 | Muijs Van De Moer et al. | |
| 6,022,351 A * | 2/2000 | Bremer | A61B 17/688 606/907 |
| 6,045,569 A | 4/2000 | Kensey et al. | |
| 6,090,130 A | 7/2000 | Nash et al. | |
| 6,860,895 B1 * | 3/2005 | Akerfeldt | A61B 17/0057 606/217 |
| 7,175,646 B2 | 2/2007 | Brenneman et al. | |
| 7,250,057 B2 | 7/2007 | Forsberg | |

(Continued)

OTHER PUBLICATIONS

International Search Report, Feb. 4, 2021; 3 pages.
International Written Opinion; Feb. 4, 2021; 5 pages.

*Primary Examiner* — Tuan V Nguyen
(74) *Attorney, Agent, or Firm* — Michael L. Leetzow PLLC

(57)     ABSTRACT

A seal assembly that seals opening in the wall of a blood vessel has a first sealing element for placing inside the lumen of the blood vessel and to engage the interior wall surface, a shaft integrally formed with the first sealing element and fixed in a predetermined configuration relative to the first sealing element, an outer floating element slidingly movable along the shaft; and a second sealing element, the second sealing element slidingly movable relative to the first sealing element along the shaft to engage the outer floating element and position the outer floating element against the exterior surface and the first sealing element against the interior surface of the blood vessel to seal the opening in the blood vessel.

15 Claims, 30 Drawing Sheets

(56)                    References Cited

U.S. PATENT DOCUMENTS 7,335,220  B2      2/2008   Khosravi et al.
        7,488,340  B2      2/2009   Kauphusman et al.
        7,597,705  B2     10/2009   Forsberg et al.
        7,618,438  B2     11/2009   White et al.
        7,850,710  B2     12/2010   Huss
        7,931,670  B2      4/2011   Fiehler et al.
        7,988,706  B2      8/2011   Forsberg
        8,029,533  B2     10/2011   Bagaoisan et al.
        8,048,108  B2     11/2011   Sibbitt, Jr. et al.
        8,075,589  B2     12/2011   Pipenhagen et al.
        8,080,034  B2     12/2011   Bates et al.
        8,097,016  B2 *    1/2012   Djurovic ............ A61B 17/0057
                                                              606/213
        8,128,632  B2      3/2012   Paris et al.
        8,128,652  B2      3/2012   Paprocki
        8,128,653  B2      3/2012   McGuckin, Jr. et al.
    2001/0007077  A1      7/2001   Ginn et al.

2002/0002386  A1      1/2002   Ginn et al.
    2003/0078598  A1      4/2003   Ginn et al.
    2006/0142797  A1      6/2006   Egnelov et al.
    2006/0195123  A1      8/2006   Ginn et al.
    2006/0195124  A1      8/2006   Ginn et al.
    2006/0206146  A1      9/2006   Tenerz
    2006/0265007  A1     11/2006   White et al.
    2006/0271078  A1     11/2006   Modesitt
    2007/0060895  A1      3/2007   Sibbitt, Jr. et al.
    2007/0185529  A1      8/2007   Coleman et al.
    2008/0109030  A1      5/2008   Houser et al.
    2008/0243182  A1     10/2008   Bates et al.
    2009/0177225  A1 *    7/2009   Nunez ................. A61B 5/6862
                                                              606/213
    2009/0254119  A1     10/2009   Sibbett, Jr. et al.
    2010/0087854  A1      4/2010   Stopek et al.
    2010/0305601  A1     12/2010   Karbowniczek et al.
    2011/0066181  A1      3/2011   Jenson et al.
    2012/0022585  A1      1/2012   Atanasoska et al.
    2014/0025103  A1      1/2014   Hundertmark et al.

* cited by examiner

VESSEL SEALING DEVICE

BACKGROUND OF THE INVENTION

This application is a continuation application of application Ser. No. 16/429,969, filed on Jun. 3, 2019, which in turn is a continuation application of application Ser. No. 14/861, 485, filed on Sep. 22, 2015, which is a continuation-in-part application of application Ser. No. 13/746,278, filed on Jan. 21, 2013, issued on Sep. 22, 2015 as U.S. Pat. No. 9,138, 215, the contents of which are incorporated by reference in their entirety.

FIELD OF THE INVENTION

The present invention relates generally to a sealing device for the closure of puncture holes in blood vessels and, in particular, to a sealing device that does not require a sheath change and is simple to operate.

TECHNICAL BACKGROUND

For many diagnostic and interventional procedures it is necessary to access arteries or veins. Vessel access is accomplished either by direct vision or percutaneously. In either case, the target vessel is punctured with a hollow needle containing a tracer wire. When the intravascular positioning of the tracer wire has been verified, the hollow needle is removed leaving the tracer wire. Next, a sheath containing a dilator is pushed in over the tracer wire. The dilator enlarges the puncture opening to facilitate the insertion of the larger diameter sheath into the blood vessel. The sheath usually consists of a hollow tube with an open distal end and a hemostatic valve at a proximal end, which remains outside the body and blood vessel. The hemostatic valve is made of a compliant material and is designed in such a way as to allow devices such as catheters to be inserted and withdrawn from the blood vessel with minimal blood loss. After the sheath has been inserted into the blood vessel, the dilator is removed leaving a clear passageway in the sheath for the catheter. The sheath is removed from the blood vessel after the procedure is finished resulting in bleeding at the puncture site that must be staunched.

Traditionally, pressure is applied at the puncture site to allow the blood to clot, thereby stopping the bleeding. Depending on the amount of anticoagulants that may have been administered to the patient during and prior to the procedure, the time that the pressure must be maintained varies from 15 minutes to more than an hour. Once bleeding has stopped, a pressure bandage is placed over the site of the puncture in an attempt to protect the integrity of the clot. The pressure bandage must remain in place for some time, usually from 8 to 24 hours. During this period of time the patient must remain in bed, sometimes requiring an overnight hospital stay.

To shorten the length of time required for the patient to become ambulatory and to lessen complications that may arise from the traditional method of sealing the opening, several closure devices have been developed. One such device, as described in U.S. Pat. No. 5,620,461, is a foldable sheet with an attachment thread that is inserted into the opening in the blood vessel and an arresting element that is applied over the attachment element against the outside of the blood vessel. Another such device is described in U.S. Pat. Nos. 6,045,569 and 6,090,130, and includes an absorbable collagen plug cinched down against an absorbable intervascular anchor via an absorbable suture. The absorbable intervascular anchor has an elongated rectangular shape that requires it to be inserted into the puncture wound with its longitudinal axis approximately parallel to the sheath axis. This requires it to be rotated ninety degrees after insertion so that blood flow obstruction is minimized. A specially designed sheath is necessary to assure proper rotation, thus resulting in an otherwise unnecessary sheath change. The long dimension of the anchor is thus larger than the cannula inside diameter (ID) and the width is smaller than the ID. The collagen plug is in an elongated state prior to deployment and is forced into a ball shape via a slipknot in the suture, which passes through the collagen, and a tamper that applies a distal force to it. The anchor acts as a support for the suture cinch which forces the collagen ball shape up against the exterior blood vessel wall and the anchor. Blood flow escaping around the anchor is slowed down and absorbed by the collagen material and thus forms a clotting amalgamation outside the blood vessel that is more stable than the traditional method of a standalone clot. The added robustness of the amalgamation clot allows earlier ambulation of the patient.

The device raises several issues. It is not a true sealing device but rather a clotting enhancement device, as opposed to a device with two flat surfaces exerting sealing pressure on both the interior and exterior of the blood vessel, a much more reliable technique. In either case, bleeding occurs during the time between removal of the sheath and full functionality of the deployed device. Thus "instant" sealing pressure from two flat surfaces is desirable over a method that relies to any extent on clotting time. One such device is disclosed by Bates et. al. in U.S. Pat. No. 8,080,034. The '034 device comprises an internal sealing surface pivoting on a rigid post to accommodate the longitudinal dimension of the seal inside the sheath ID. The exterior seal (second clamping member) is slidable along the rigid post and pivotal such that it, along with the internal seal, sandwiches the wall of the blood vessel via a locking ratchet. One problem with this design is that the pivoting feature increases the cross-sectional dimension of the seal thus requiring a larger diameter sheath than would be otherwise needed. In addition, the pivoting internal seal has no means to assure that the seal pivots to the correct sealing position as the ratchet closes. This could cause the internal seal to exit the blood vessel in the collapsed configuration as the user withdraws the deploying device. In addition no specific mechanism for the release of the seals from the deployment instrument is disclosed, other than a general statement "any known means."

The seals are released by the user cutting the suture thread in the device described in U.S. Pat. No. 6,045,569.

It is known that the opening in the blood vessel closes to some extent after the sheath is removed, thus allowing smaller seal surfaces than would otherwise be required. What is less known is that the opening does not close as quickly as a truly elastic material such as natural rubber or latex. For this reason, seal surfaces of closure devices that are activated in less than a second, or perhaps even longer, after sheath removal must be physically larger than the sheath outside diameter to avoid embolization of the seals because of the delayed blood vessel closure. The design of seals that are deployed through a sheath ID with dimensions larger than the sheath OD upon deployment is a challenge since the preferred material for seals are bio-absorbable and thus have limited mechanical properties.

An active sealing assembly comprising solid, flat interior and exterior elements that sandwich the blood vessel wall to insure hemostasis and yet have major dimensions that exceed the interior diameter of the introducer sheath to compensate for slow, partial closure of the wound upon removal of the sheath thereby minimizing leakage and avoiding embolization of the sealing components offers a design challenge. Components can be introduced through the sheath internal diameter (ID) longitudinally and rotated into a position adjacent to the blood vessel wall such that the longitudinal dimension exceeds the sheath ID with little or no concern regarding the mechanical properties of the material. The devices in the '461 and '034 patents are examples. As noted previously, these solutions have severe limitations.

Another method of accomplishing the desired result of obtaining a deployed seal larger than the sheath ID is to fold the seal elements while they traverse the sheath ID and reopen them upon deployment. Optimally, the major dimension of the seal elements should be 1.5 to 2 times larger than the outside diameter of the sheath. The '569 Patent discloses an external seal made of an elongated pliable collagen plug that swells upon absorbing blood leaking from the wound and is tamped into more or less of a ball larger than the opening of the wound. The internal seal is inserted longitudinally through a special sheath which, with the aid of an attachment thread, rotates the seal parallel to the blood vessel surface.

The '569 device requires removing the catheter sheath and replacing it with a custom sheath prior to deployment, resulting in additional blood loss. The tamping force used to deploy the collagen against the anchor is left to the surgeon's feel, sometimes resulting in inadequate deployment and other times resulting in the collagen being pushed through the puncture wound and into the blood vessel along with the anchor. Inadequate tamping results in excessive bleeding with the potential for painful hematoma and over tamping can require a surgical procedure to remove the device from the blood vessel lumen. In addition, the absorption rate of the suture, the collagen, and the anchor may be different owing to the fact that they are formed from different materials, sometimes resulting in the premature detachment of the anchor, which can move freely in the blood stream and become lodged in the lower extremities of the body, again requiring surgical removal.

U.S. Pat. No. 5,350,399 discloses umbrella-shaped foldable bio-compatible seals that are not bioabsorbable.

It would be desirable therefore to provide a vessel-sealing device that actually seals the blood vessel and does not rely on the clotting of the blood. It is also desirable to provide a closure device that is deployable through the catheter sheath with minimal steps requiring less than 2 minutes for hemostasis. It would be also desirable to provide a reliable, active vessel-sealing device comprising a bio-absorbable seal assembly with deployed major dimensions larger than the sheath outside diameter.

SUMMARY OF THE INVENTION

Disclosed herein is a seal assembly for sealing an opening in the wall of a blood vessel, the blood vessel having an interior wall surface, exterior wall surface, and a lumen, the seal assembly the includes a first sealing element for placing inside the lumen of the blood vessel, a shaft formed with the first sealing element as a single one-piece component, the shaft fixed in a predetermined configuration relative to the first sealing element, the shaft having a length sufficient to extend through the opening of the blood vessel and at least a portion of any overlying tissue, a flexible member surrounding at least a portion of the shaft adjacent the first sealing element, an outer floating element slidingly movable along the shaft, the outer floating element having a proximal surface and a distal surface, and a second sealing element, the second sealing element slidingly movable relative to the first sealing element along the shaft to engage the outer floating element and configured to position the distal surface of the outer floating element against the exterior wall surface and the flexible gasket against the interior wall surface of the blood vessel to seal the opening in the blood vessel.

In some embodiments, the flexible member is secured to a proximally facing surface of the first sealing element.

In some embodiments, the shaft has at least two sides, the at least two sides each having a groove along a portion thereof and the outer floating element has an aperture to receive the shaft therethrough, the aperture generally being rectangular and having two protrusions extending into the aperture and configured to the groove on a respective side of the shaft.

In some embodiments, each of the protrusions has a first surface capable of engaging a first wall of the groove and a second surface capable of engaging a second wall of the groove and when the first surface engages the first wall of the groove, the distal surface of the outer floating element is disposed relative to the first wall at an angle of between 35 and 55 degrees.

In other embodiments, the device includes an inserter, the inserter includes a housing have a first portion and a second portion, the first portion and second portion having a proximal end and a distal end, a longitudinal opening extending through the housing when the first and second portion are connected to one another and opening at the proximal and distal ends, and an aperture in one of the first and second portions, the aperture configured to receive a portion of the first sealing element when the first and second portion are connected to one another and the seal assembly is inserted therein.

In another aspect, the present invention is directed to method of sealing an opening in the wall of a blood vessel, the blood vessel having an interior wall surface, exterior wall surface, and a lumen, the method including providing a seal assembly for sealing the opening in the blood vessel, the seal assembly operatively connected to an insertion device and comprising a first sealing element for placing inside the lumen of the blood vessel, a shaft formed with the first sealing element as a single one-piece component, the shaft fixed in a predetermined configuration relative to the first sealing element, the shaft having a length sufficient to extend through the opening of the blood vessel and at least a portion of any overlying tissue, a flexible member surrounding at least a portion of the shaft adjacent the first sealing element, an outer floating element slidingly movable along the shaft, the outer floating element having a proximal surface and a distal surface, and a second sealing element, the second sealing element slidingly movable relative to the first sealing element along the shaft to engage the outer floating element and configured to position the distal surface of the outer floating element against the exterior wall surface and the flexible gasket against the interior wall surface of the blood vessel to seal the opening in the blood vessel, inserting a portion of the seal assembly into the lumen of the blood vessel, and retracting the seal assembly and insertion device until the first seal element and flexible member engages the interior wall surface of the blood vessel and causes the insertion device to automatically actuate thereby pushing the second sealing element and the outer floating element toward the exterior wall surface to position the outer floating element against the exterior surface and causing the shaft to break at a reduced portion disposed within the shaft.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description of the present embodiments of the invention are intended to provide an overview or framework for understanding the nature and character of the invention as it is claimed. The accompanying drawings are included to provide a further understanding of the invention and are incorporated into and constitute a part of this specification. The drawings illustrate various embodiments of the invention and, together with the description, serve to explain the principles and operations of the invention.

DETAILED DESCRIPTION OF THE PREFERRED EMBODIMENTS

Figure 1:
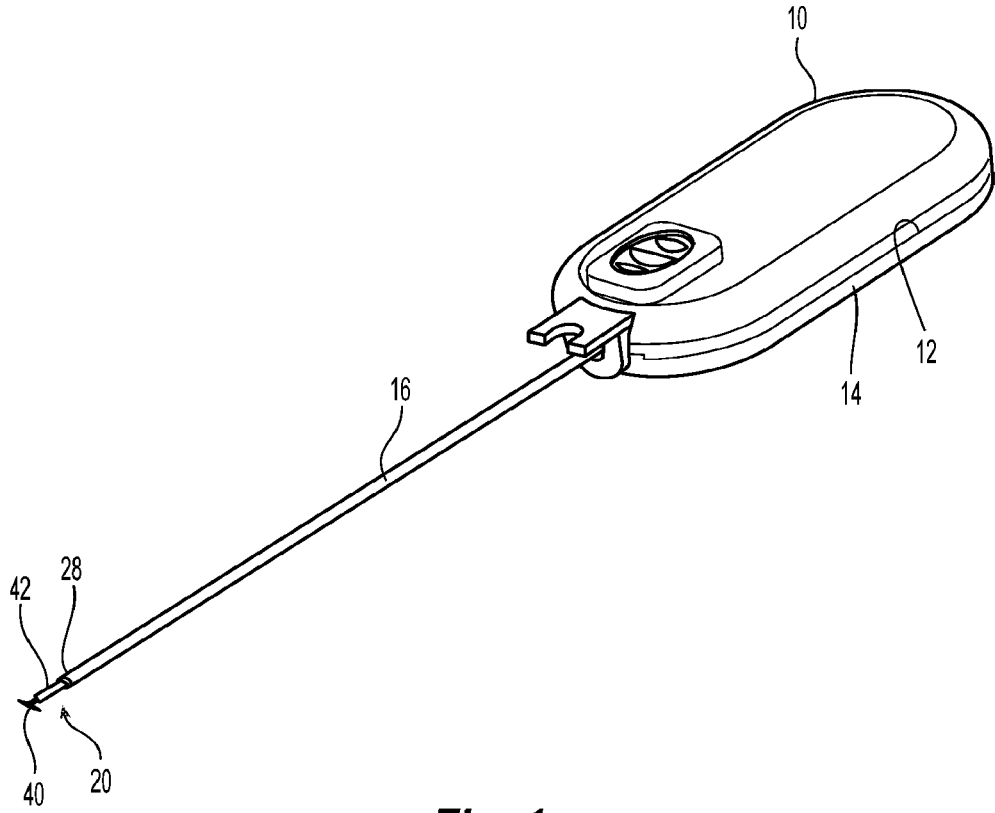
FIG. 1 is a perspective view of one embodiment of a sealing device according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Figure 2:
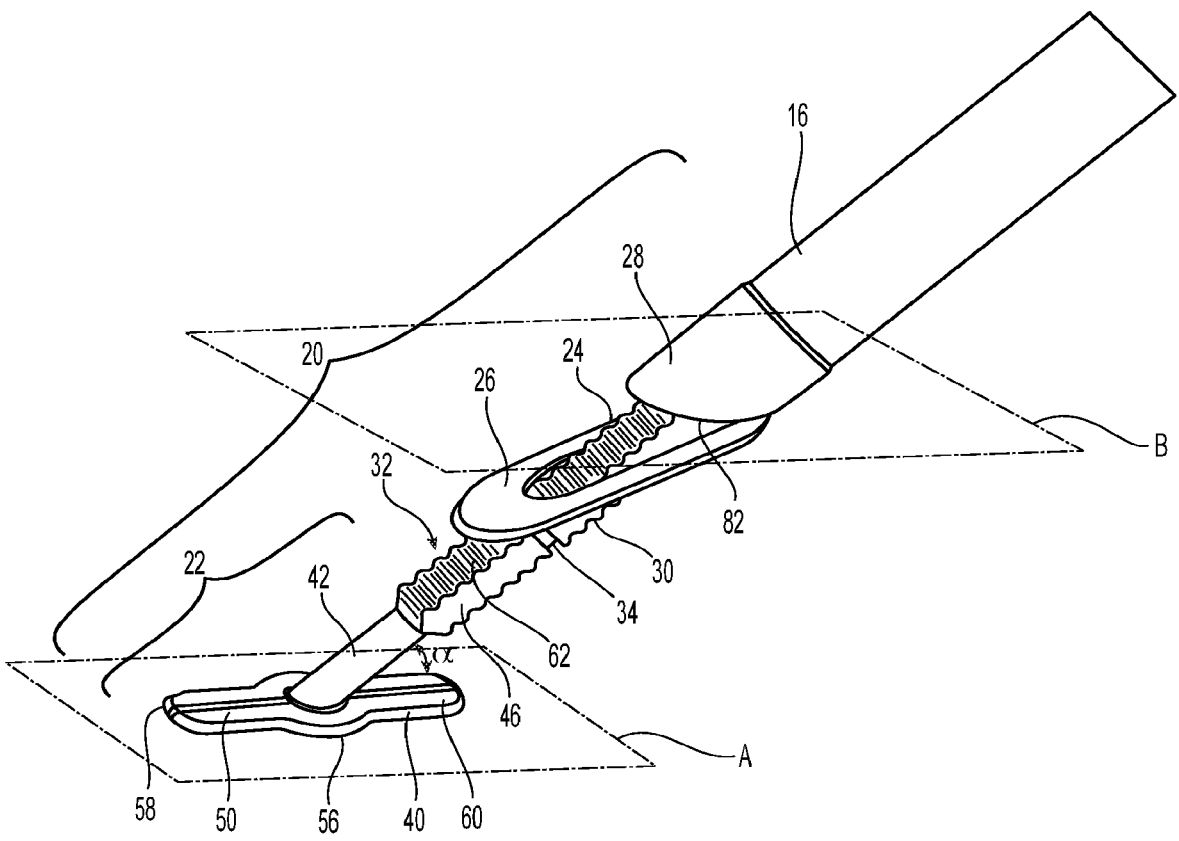
FIG. 2 is a perspective view of a portion of the sealing device of FIG. 1 illustrating the seal assembly thereof.

Referring to FIGS. 1 and 2, closure device 10 comprises two handle halves 12,14 housing an automatic mechanism detailed in co-pending application titled "Vessel Sealing Device with Automatic Deployment," and assigned Ser. No. 13/746,276, the contents of which are incorporated herein by reference in their entirety. The automatic mechanism is coupled to the seal assembly 20 by a flexible pusher 16 and a flexible shaft 18. See also FIG. 6. Seal assembly 20 has a first sealing element 22, a knobbed rigid shaft 24, an outer floating element 26, and a second sealing element 28. Knobbed, rigid shaft 24 has a proximal section 30 and a distal section 32 separated by a weakened notch feature 34, which is configured to separate seal assembly 20 from the rest of the closure device 10 once the automatic deployment and sealing process is complete. The length of the distal section 32 of knobbed shaft 24 is dictated by the thickness of the vessel wall that can be accommodated (see FIG. 10). The first sealing element 22 also has a distal section 40 configured to interface with the inside wall of a vessel to be sealed (see also FIG. 9), a knobbed, rigid distal shaft section 32 (which is a part of the knobbed, rigid shaft 24), and ankle section 42 joining the distal section 40 to the knobbed, rigid distal shaft section 32. The ankle section 42 is attached to distal section 40 at an angle α, which is preferably at an angle of about 45°. Although other angles may be used, the value of angle α may cause other values of the seal assembly to be changed, as discussed in detail below.

A more detailed view of the first sealing element 22 and the knobbed rigid shaft 24 are illustrated in FIGS. 3A-3D. The first sealing element 22 has the distal section 40, ankle section 42 and the knobbed, rigid distal shaft section 32. The distal section 40 has a proximal or top surface 50, a bottom surface 52 and an outer peripheral surface 56. The proximal or top surface 50 is preferably configured to engage the interior wall surface 142 of the blood vessel 140 (see FIG. 9), which means that the top surface 50 is preferably flat. However, the top surface 50 can be of any configuration (e.g., flat, convex, etc) and still come within the scope of the present invention. The bottom surface 52 is preferably flat, but may have other configurations. As noted below, the exact configuration of the surfaces 50,52 may also depend on the strain that is placed on them prior to and during insertion. The outer peripheral surface 56 is preferably continuous in that it has no discontinuities. That is, the outer peripheral surface 56 is smooth and has no sharp angles (e.g., 30, 45 or 90° angles). Since the distal section 40 is to be deformed prior to insertion into the blood vessel 140, any sharp angles tend to create stress points, potentially causing the distal section 40 to be bent/deflected beyond its ability to return to its original configuration. The distal section 40 has a thickness that increases from the front (or distal) end 58 to the rear (or proximal) end 60. In the embodiment illustrated in the figures, the thickness increases from 0.28 mm at the front end 58 to 0.30 mm at the rear end 60. However, other thicknesses and tapered shapes fall within the scope of the present invention.

Figure 3A:
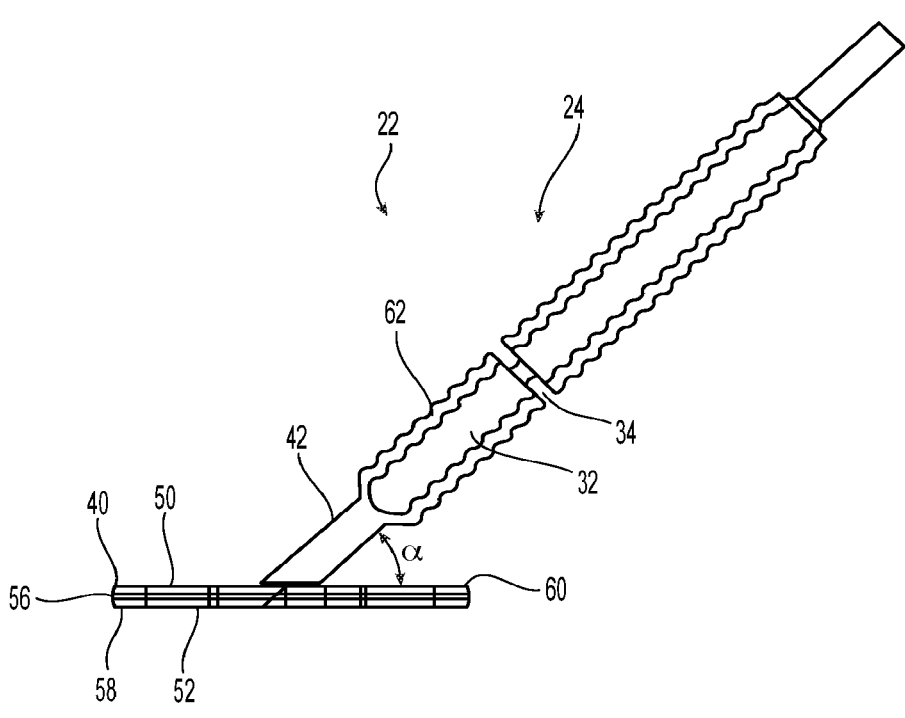
FIG. 3A is a side plan view of the first sealing element and the shaft.
Figure 3B:
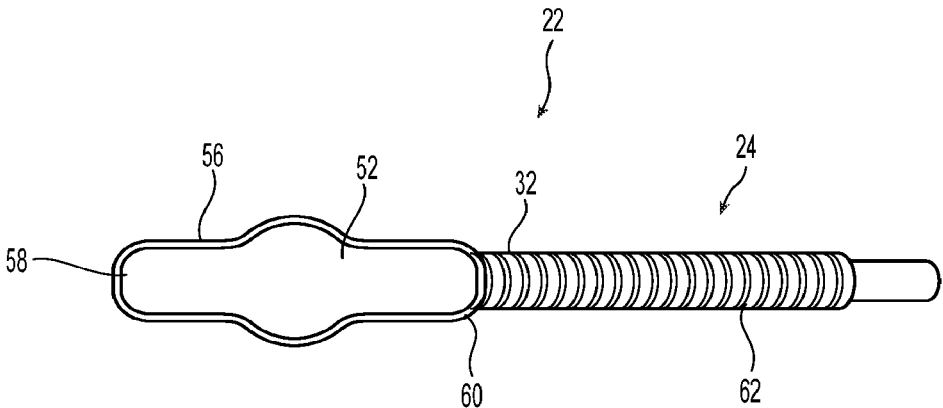
FIG. 3B is a bottom plan view of the first sealing element and the shaft.
Figure 3C:
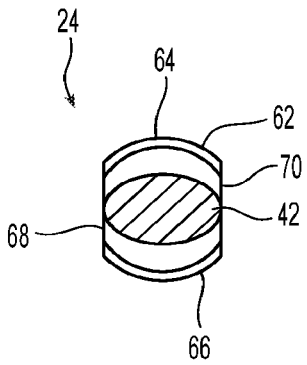
FIG. 3C is a cross section view of the shaft at the location of the reduced portion.
Figure 3D:
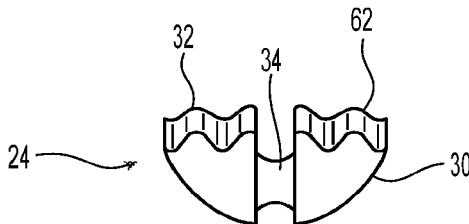
FIG. 3D is a partial side view of the shaft at the location of the reduced portion.

Illustrated in FIGS. 3C and 3D are a cross section of the knobbed rigid shaft 24 at the ankle 42 and partial side view of the knobbed rigid shaft 24 showing the weakened notch feature 34, respectively. The cross section of the ankle 42 in FIG. 3C illustrates the shape of the ankle 42, the knobs 62 on the upper 64 and the lower 66 surface, and the smooth sides 68,70 of the knobbed rigid shaft 24, which cooperates with the other portions of the first sealing element 22 to ensure that the outer floating element 26 and the second sealing element 28 are properly positioned, as discussed in more detail below.

Figure 6:
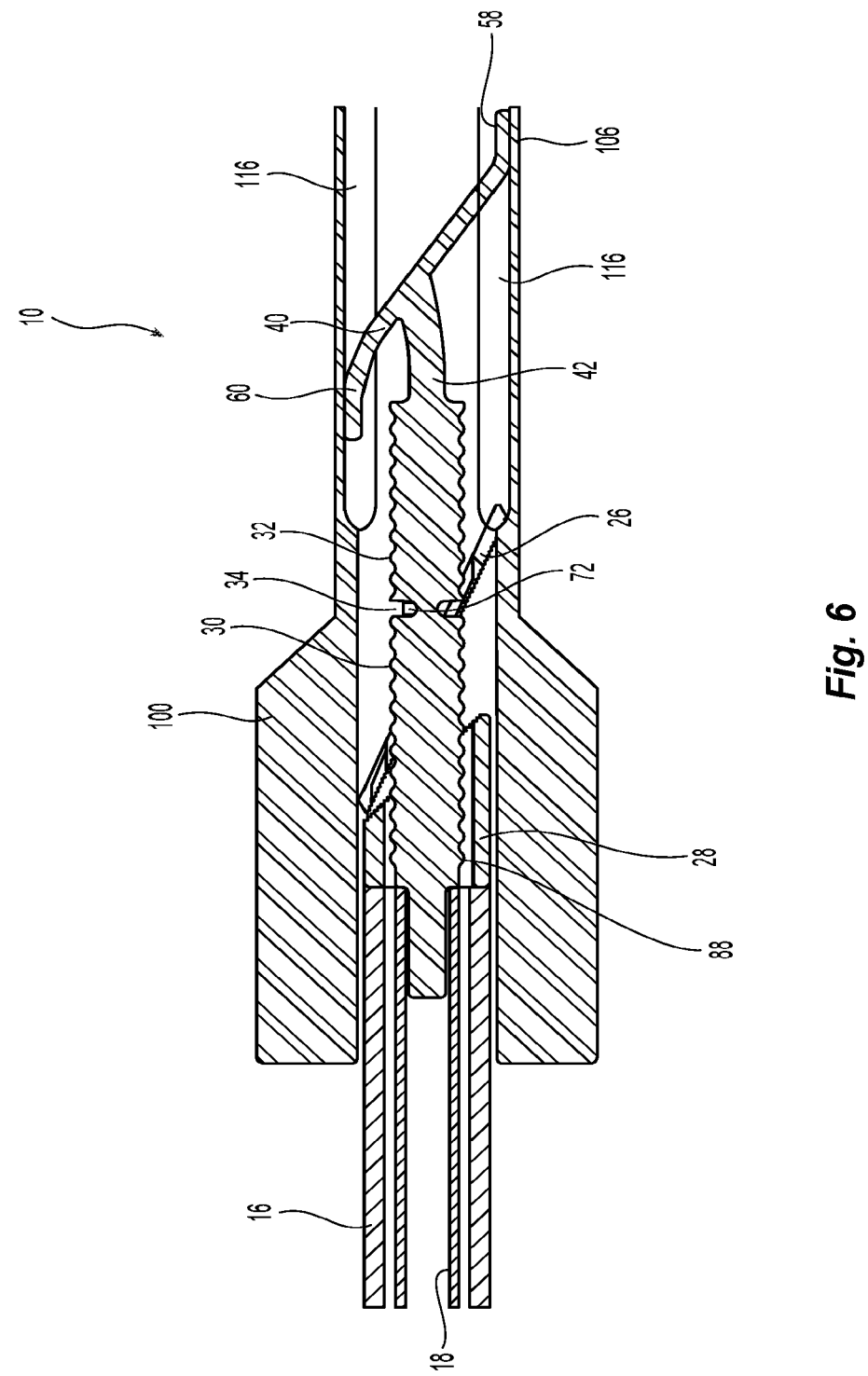
FIG. 6 is a cross section view of the seal assembly constrained in a sheath introducer.

The weakened notch feature 34 is illustrated in FIG. 3D. The weakened notch feature 34 has a smaller cross section than any other portion of the knobbed rigid shaft 24. This allows for the knobbed rigid shaft 24 to be broken at this point upon activation of the insertion device in the co-pending application by exerting a force in the direction of the length of the knobbed rigid shaft 24, causing the knobbed rigid shaft 24 to break at the weakened notch feature 34. In order to prevent the weakened notch feature 34 from breaking prematurely, a c-shaped ring 72 is clipped into the weakened notch feature 34, as illustrated in FIG. 6. The width of notch feature 34 is sized to equal the space between knobs 62 so that second seal 28 can easily transition over notch feature 34 upon automatic activation of device 10. The c-shaped ring 72 prevents the knobbed rigid shaft 24 from being tilted off center and breaking prematurely. The c-shaped ring 72 is preferably made from a bio-absorbable material since the c-shaped ring 72 can separate from both the proximal section 30 and the distal section 32 of the knobbed rigid shaft 24 upon breaking of the weakened notch feature 34 and there is no efficient way to retrieve it from the patient.

Figure 4B:
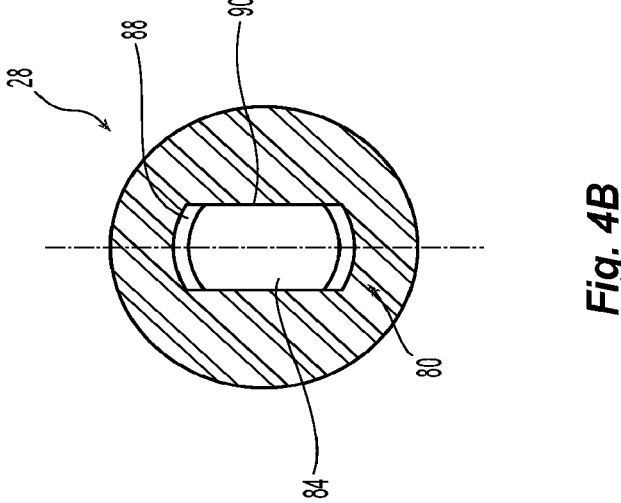
FIG. 4B is a cross section view of the second sealing element of the seal assembly of FIG. 2 that is orthogonal to the view in FIG. 2.
Figure 4A:
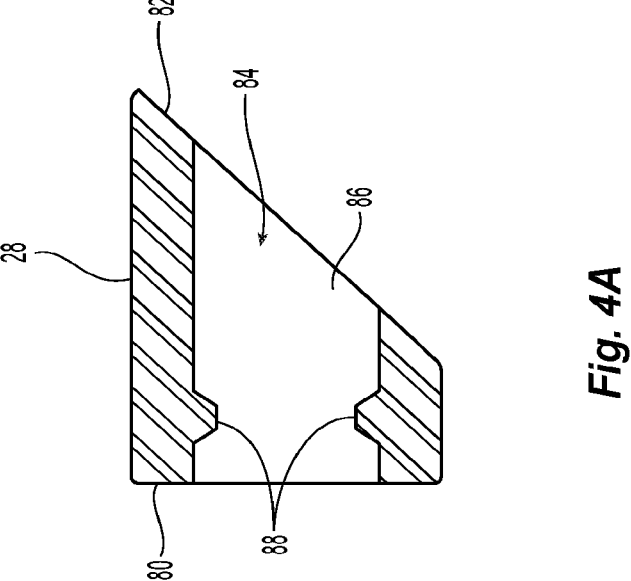
FIG. 4A is a cross section view along a longitudinal axis of a second sealing element of the seal assembly of FIG. 2.

Second sealing element 28 is shown in more detail in FIGS. 4A and 4B. The second sealing element 28 has a proximally facing surface 80 and a sloped distally facing surface 82. An internal opening 84 defined by the internal surface 86 extends between the proximally facing surface 80 and the sloped distally facing surface 82. The internal surface 86 has extending therefrom and into the internal opening 84 projections 88 that interface with and engage the knobs 62 with an interference fit such that second sealing element 28 and knobbed rigid shaft 24 function as a one way latch assuring an adequate compression force regardless of the blood vessel wall thickness.

As can be best seen in FIG. 2, the proximal or top surface 50 of first sealing element 22 lies in a first plane A and the sloped distally facing surface 82 of second sealing element 28 lies in a second plane B. Preferably, the first plane A and the second plane B are parallel to one another.

Referring to FIG. 4B, the internal opening 84 of second sealing element 28 (and floating foot 26) have two flat surfaces 90 on opposite sides of the internal opening 84 that interface with flat surfaces 68,70 of knobbed rigid shaft 24 to provide rotational stability of the seal assembly components 26,28 thus assuring that the sloped distally facing surface 82 and the fully deployed floating foot 26 remain parallel with the distal section 40 of the first sealing element 22 and the proximal or top surface 50 in particular.

Figure 5A:
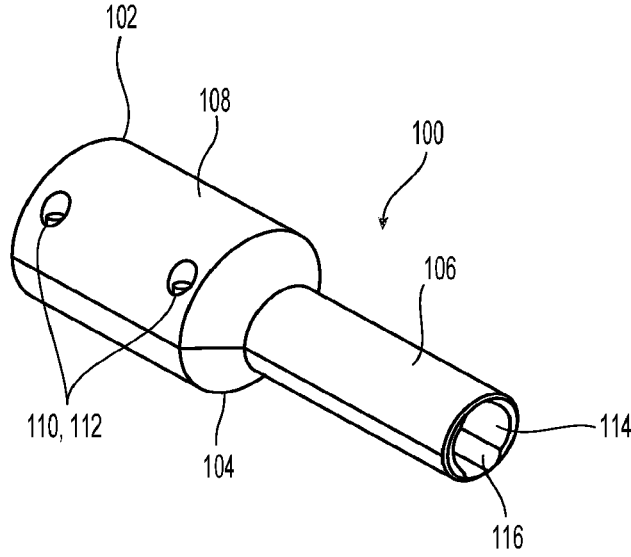
FIG. 5A is a perspective view of a sheath introducer used with the sealing device of FIG. 1.
Figure 5B:
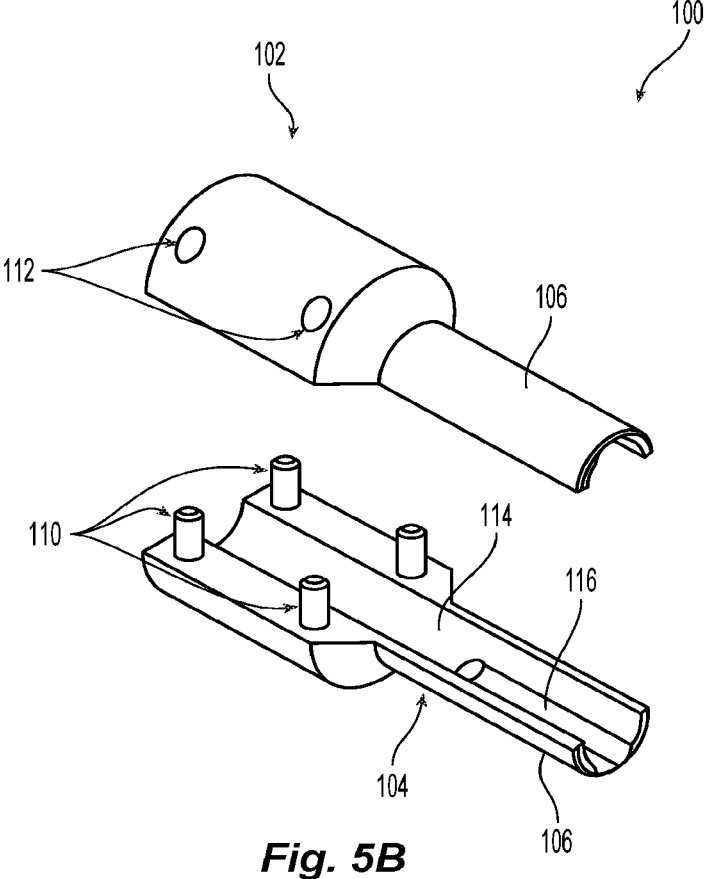
FIG. 5B is an exploded, perspective view of the sheath introducer of FIG. 5A.

FIGS. 5A and 6B depict introducer or outer sleeve 100, which is configured to protect seal assembly 20 from damage when inserting seal assembly 20 through a hemostatic valve, which, as discussed below and in more detail in the co-pending application, is one method in which the seal assembly is inserted into the patient. Introducer 100 comprises two halves, 102,104, which when assembled together form a generally cylindrical body having two different diameters. Front section 106 of introducer 100 has a smaller diameter than rear section 108. Front section 106 with the smaller diameter is configured to be inserted into hemostatic valve and rear section 108, having the larger diameter remains proximal to the hemostatic valve. While the two halves 102,104 can be assembled according to any typical manner, pins 110 on one of the two halves 102,104 are configured with a press fit into corresponding mating holes 112 thus holding halves 102,104 firmly together.

Figure 7:
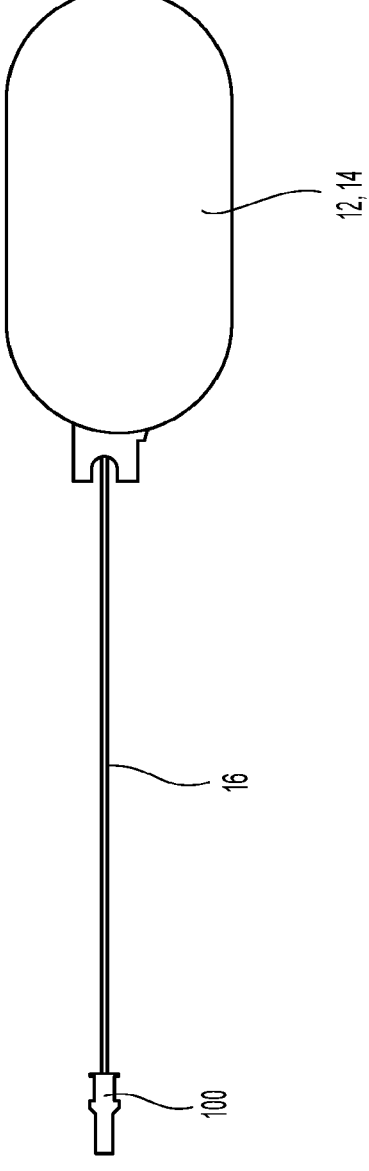
FIG. 7 is a top view of the sealing device with the sheath introducer of FIG. 5A.

The introducer 100 has an opening 114 that extends between the front section 106 and the rear section 108. However, within the opening 114 are also grooves 116 that are configured to accept seal assembly 20. The opening 114 is also configured to receive at least a portion of pusher 16 of the seal device 10. FIG. 6 is a cross section of seal assembly 20 in the initial position inside introducer 100 prior to insertion into a sheath 120. The front end 58 and the rear end 60 of the distal portion 40 of first sealing element 22 are deformed into a configuration such that the distal portion 40 of first sealing element 22 is able to pass through the inside dimension of cannula 122 upon insertion of closure device 10 resulting in the configuration shown in FIG. 6. The initial position of introducer 100 is shown in FIG. 7. After exit from distal end of cannula 122, the front end 58 and the rear end 60 of the distal portion 40 of first sealing element 22 return to the initial configuration as shown in FIG. 2 owing to the configuration shown in FIG. 6 not exceeding the elastic limit of the material from which the seal assembly 20 is constructed.

Figure 8:
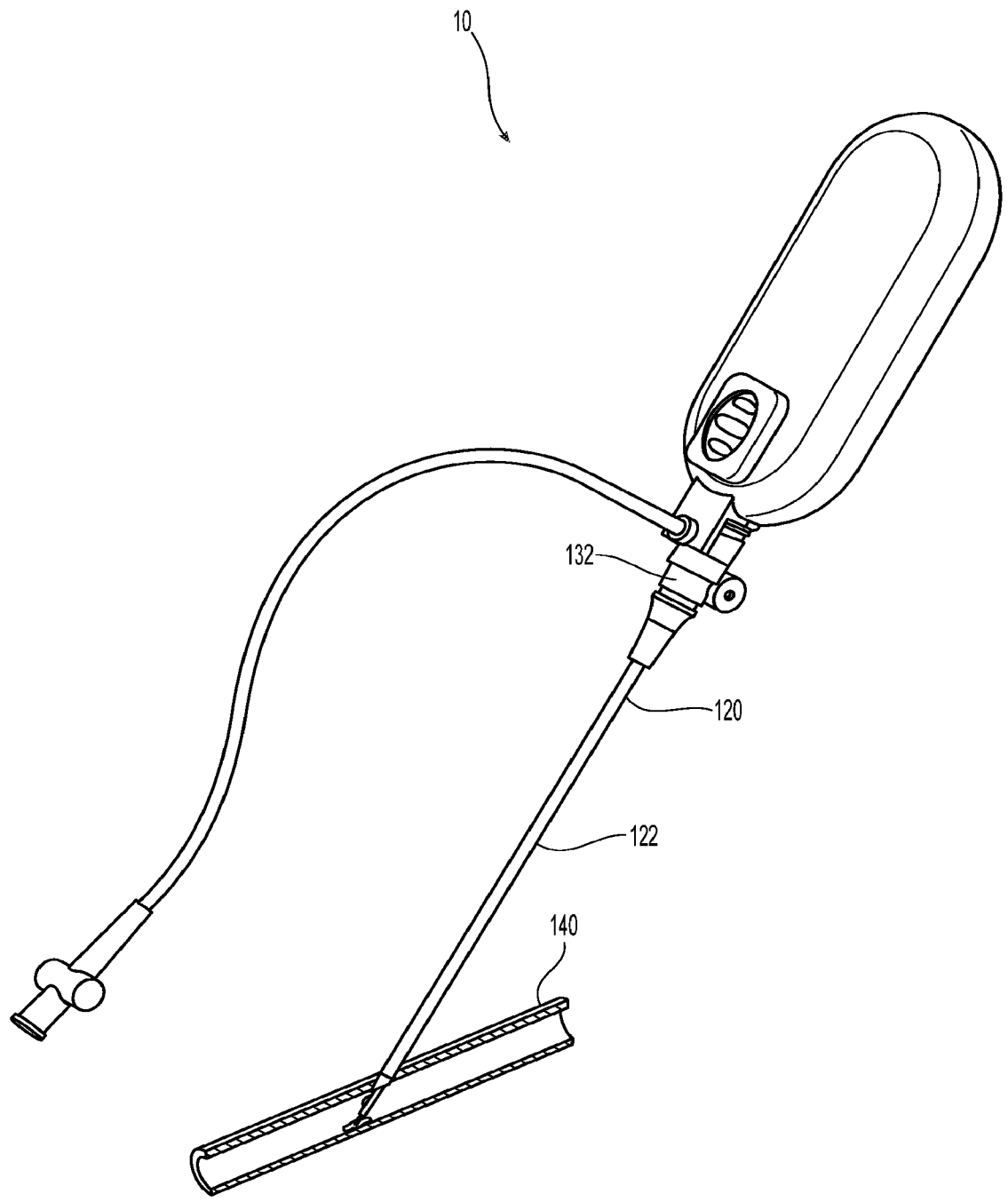
FIG. 8 is a perspective view of the sealing device inserted into a blood vessel.

FIG. 8 depicts closure device 10 inserted into sheath 120, the distal end of which is inside blood vessel 140. Proximal end of sheath 120 comprises hemostatic valve 132 attached to a funnel shaped section transitioning into cannula 122 at the distal end.

Figure 9:
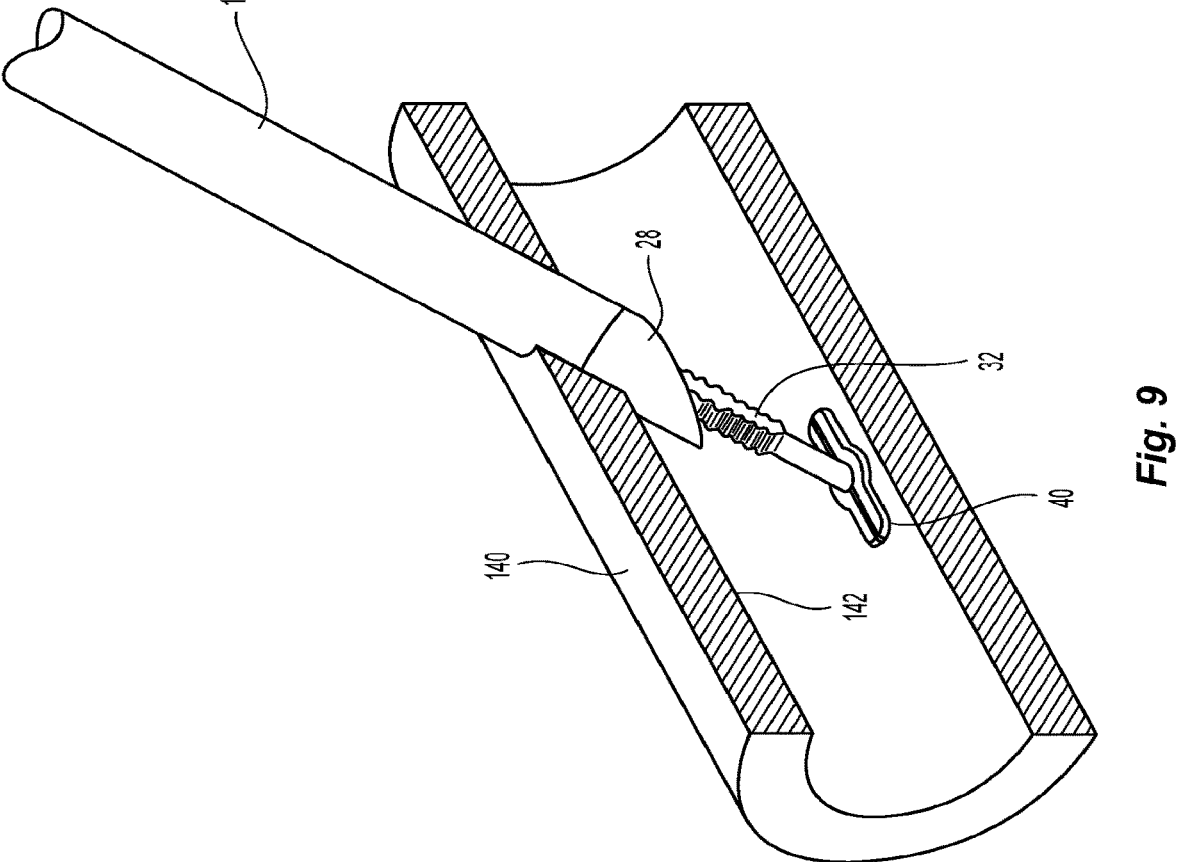
FIG. 9 is partial cross section view of a vessel with the sealing device inserted therein.
Figure 10:
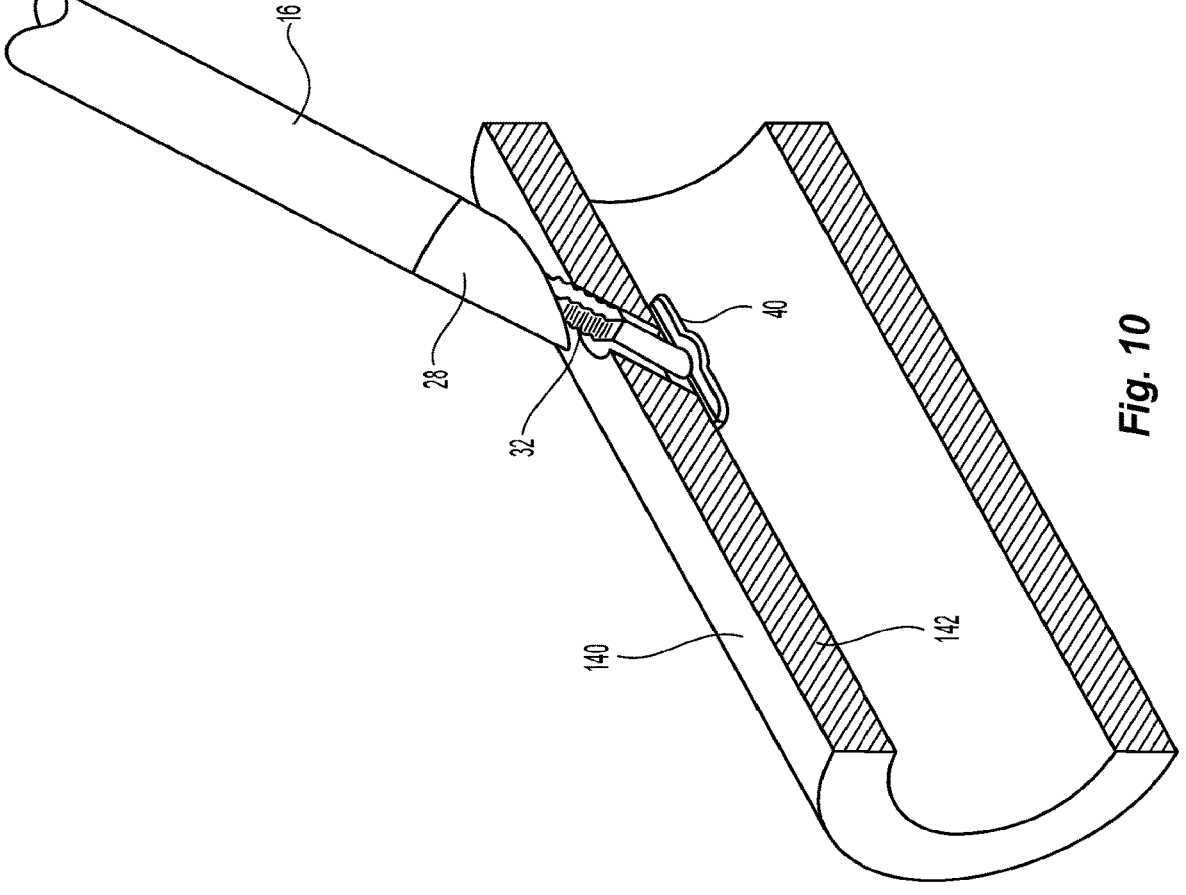
FIG. 10 is perspective view of the sealing device inserted into the blood vessel just before the sealing device is activated.
Figure 11:
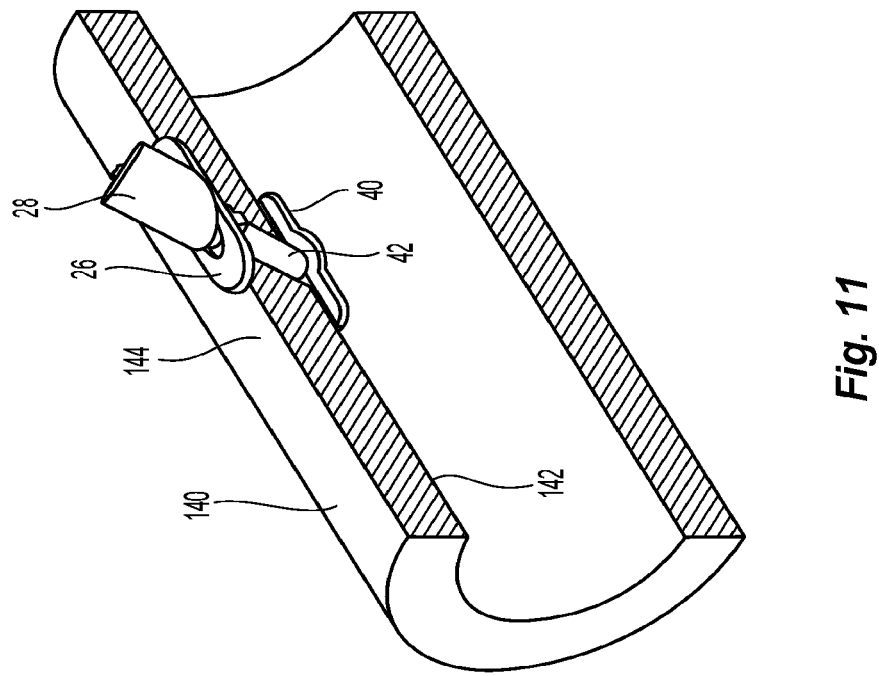
FIG. 11 is a perspective view of the seal assembly blocking the opening in the blood vessel after activation of the sealing device.

A method of using the current invention, in conjunction with FIGS. 9-11, is as follows: providing a sheath introducer 100 that surrounds and deforms seal assembly 20 such that seal assembly seal 20 can pass through sheath valve 132. See also FIGS. 6 & 8. Inserting pusher 16 through sheath 120, including valve 132 and cannula 122, causes at least a portion of seal assembly 20 to exit the distal end of cannula 122 and into blood vessel 140. A portion of the second sealing element 28 and the pusher 16 may be disposed within the blood vessel 140. See FIG. 10. Pulling on the closure device 10, the proximal or top surface 50 of the distal portion 40 of first sealing element 22 engages the interior blood vessel wall 142. This would also remove the second sealing element 28 and the pusher 16 from within the blood vessel 140. See FIG. 10. Continuing to pull on the sealing assembly 20 triggers an automatic mechanism in the closure device 10, which pushes pusher 16, and which in turn pushes second sealing element 28, and floating foot 26 (if present) distally such that floating foot 26 is in contact with outer wall of blood vessel 140. This will sandwich the second sealing element 28 against floating foot 26, blood vessel 140 and distal portion 40 of first sealing element 22 such that the opening in blood vessel 140 is hemostatically sealed, as shown in FIG. 11.

Figure 12:
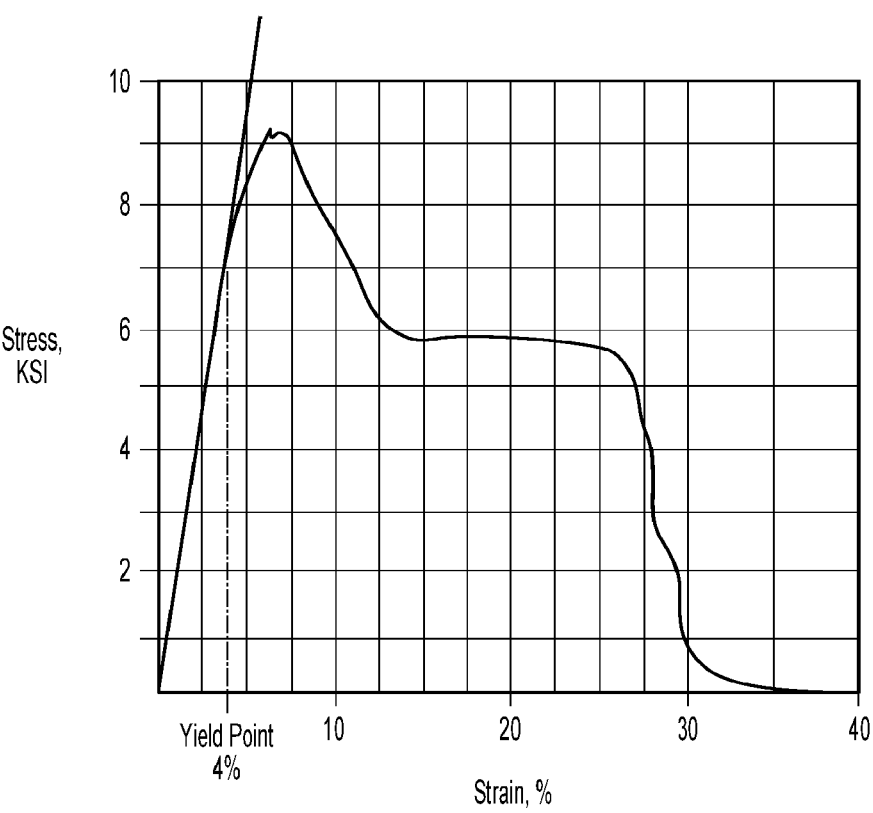
FIG. 12 is a stress-strain curve that illustrates the maximum strain without permanent deformation (yield point) is 4% for materials used in the seal assembly of FIG. 1.

To configure distal portion of first sealing element 22 such that the elastic limit of the bio-absorbable material is not exceeded when deformed in introducer 100 and deployed through cannula 122, material studies were undertaken. Bio-absorbable materials comprising different mole ratios of Lactide and Glycolide are commonly used for molded implant parts. These materials exhibit different properties such as glass transition temperature and absorption time; however the initial strength and flexibility are similar. As an example, molded samples 1.6 mm thick by 4 mm wide by 10 mm long of 85:15 L-Lactide:Glycolide with inherent viscosity of 2.1 dl/gm were tested in an Instron® Universal Tensile testing Machine Model 3340 according to ASTM E-8M-04 Standard at a crosshead speed of 2 inches/minute. A typical example of the stress strain curve is shown in FIG. 12. Of particular interest is the fact that the maximum strain without permanent deformation (yield point) is seen to be 4% for materials of this type and particularly for 85:15 L-Lactide:Glycolide with inherent viscosity of 2.1 dl/gm. Therefore, to assure no permanent deformation occurs for seal assembly 20 the maximum strain while undergoing insertion into the blood vessel through sheath 120 must be below 4%. It is worth noting that the yield point was independent of sterilization radiation level up to 50 KGy the maximum strain at break decreased with radiation level however.

Figure 13A:
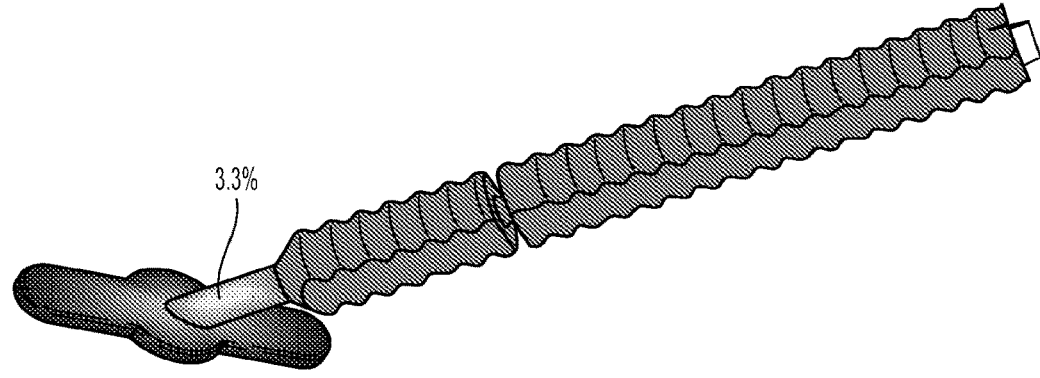
FIG. 13A illustrates a representation of strain that would be introduced into the first sealing element on the top side thereof if constrained in the sheath introducer of FIG. 5A.
Figure 13B:
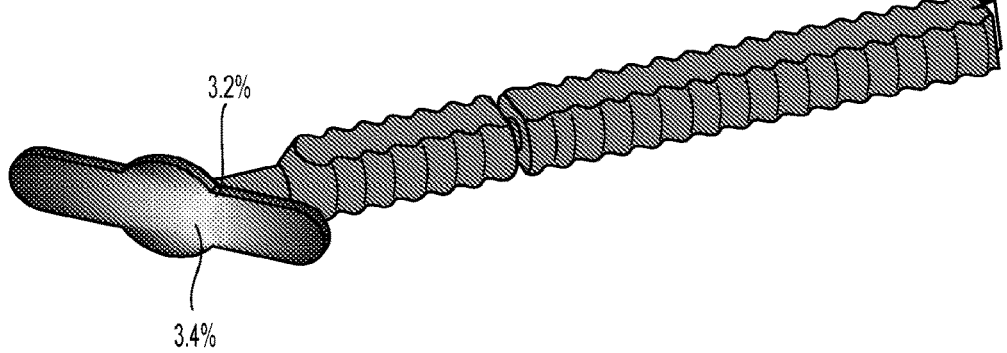
FIG. 13B illustrates a representation of strain that would be introduced into the first sealing element on the bottom side thereof if constrained in the sheath introducer of FIG. 5A.
Figure 13C:
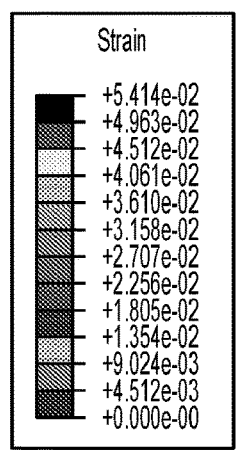
FIG. 13C is a legend for the strain representations of the first sealing element constrained in the introducer.
Figure 14:
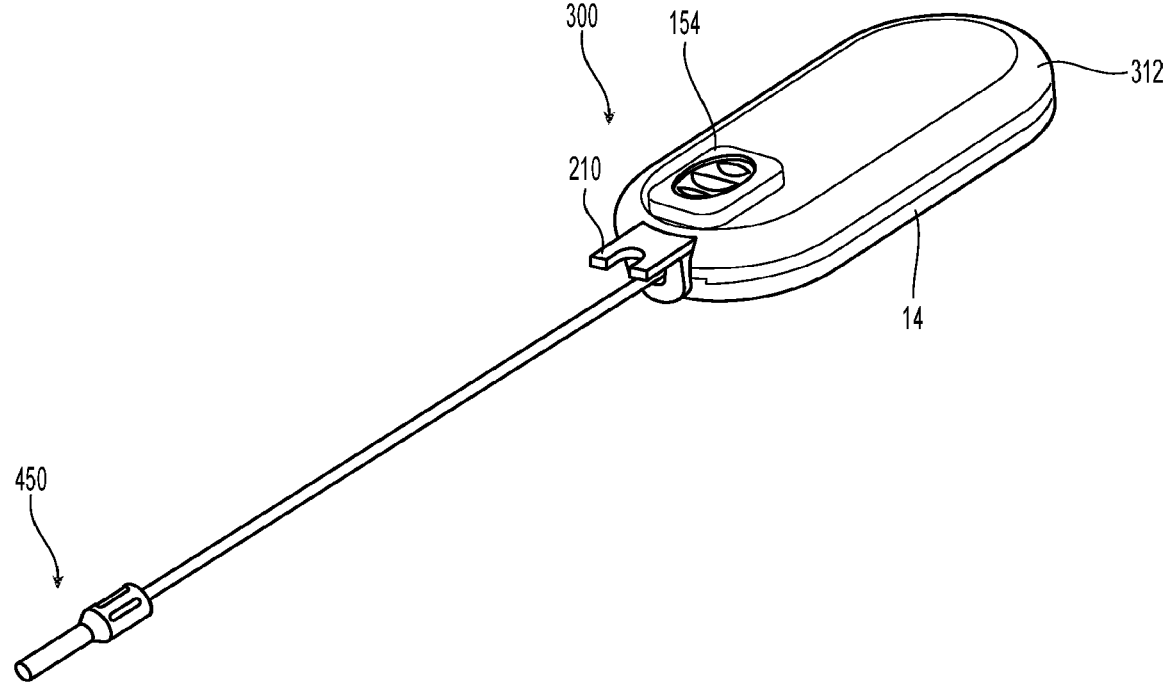
FIG. 14 is a perspective view of another embodiment of a sealing device according to the present invention.

The strain induced into a sample under different stress loads is dependent on the material basic mechanical properties but as importantly the geometric configuration. From a practical stand point closure devices are most often used in 6 French or smaller sheaths for cardiac procedures and up to 18 French or larger for AAA procedures. It is noted that when the first sealing element 22 for a 6 French closure device, is molded from 85:15 L-Lactide:Glycolide with inherent viscosity of 2.1 dl/gm, the present design stays within the strain limits. In fact, Finite Element Analysis (FEA) of variations of the present design indicate that the continuous outer periphery and the thickness taper from 0.28 to 0.30 in distal portion of first sealing element 22, along with the oval configuration of ankle 42 are critical in keeping the strain below 4% in the deformed state inside introducer 100, given the overall size and shape of the sealing assembly. FIGS. 13A-C illustrate by a grayscale map the strain in sealing assembly 20 constrained in introducer 100. It can be seen that the maximum strain is below 4% for this configuration and material.

Turning to another embodiment, a closure device 300 is illustrated in FIGS. 14-32, comprises two handle halves 312,324 housing an automatic mechanism detailed in co-pending application titled "Vessel Sealing Device with Automatic Deployment," and assigned Ser. No. 13/746,276, the contents of which are incorporated herein by reference in their entirety. The closure device 300 is similar to the closure device disclosed in co-pending application Ser. No. 13/746, 276 and the embodiment above, with a different seal assembly 320.

Figure 15:
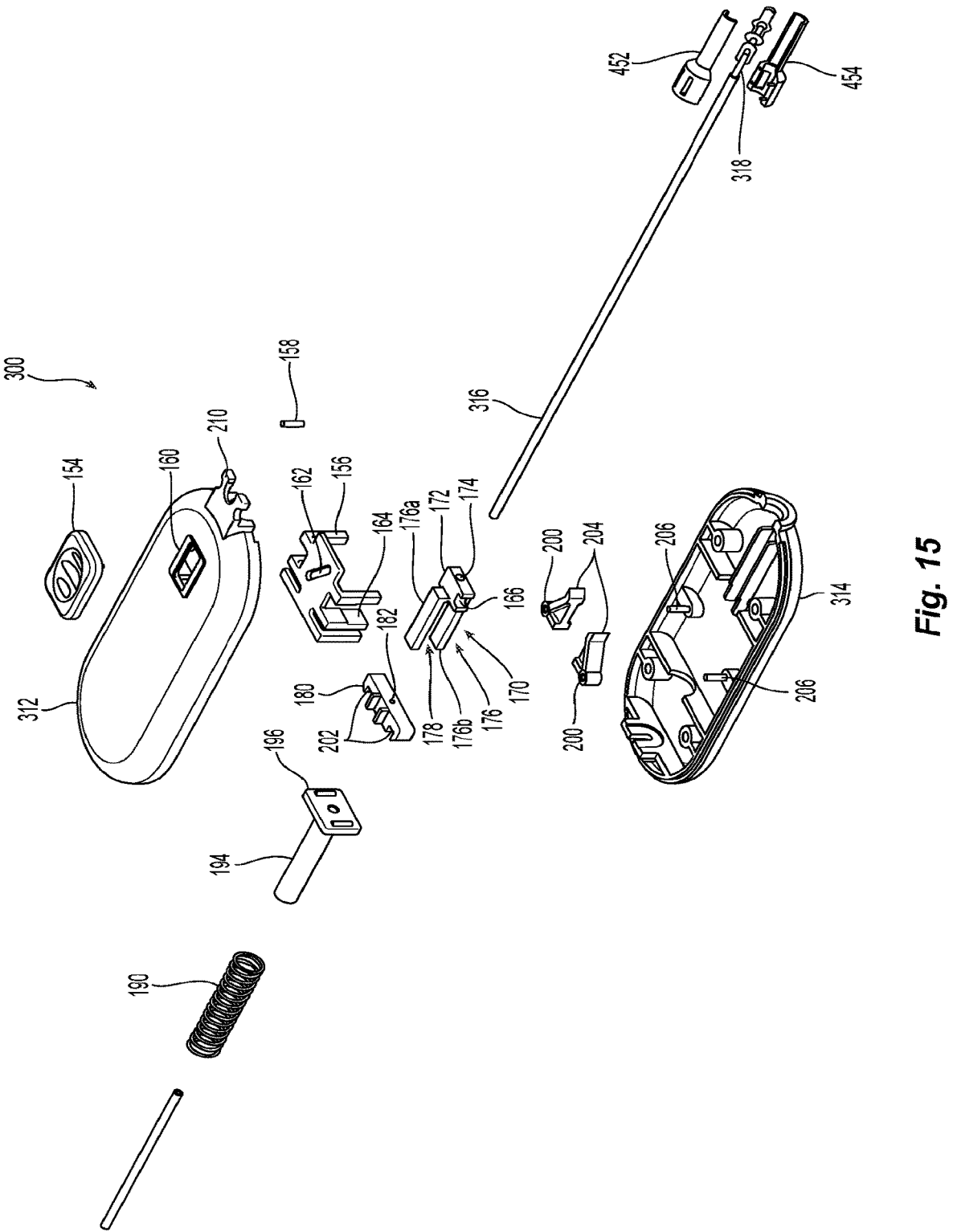
FIG. 15 is a perspective view of a portion of the sealing device of FIG. 14 illustrating the seal assembly thereof.

More specifically and referring to FIG. 15, closure device 300 comprises two handle halves 312,314 that housing automatic mechanism 150. The automatic mechanism 150 interfaces with safety latch 152, which has a safety slide 154 that interacts with safety cage 156 via pin 158. The safety latch 152 operates such that with safety slide 154 in the distal most position automatic mechanism 150 cannot be activated. The proximal most position of safety slide 154 allows automatic activation. The pin 158 is in the center of the underside of safety slide 154 and passes through handle opening 160 of handle half 312 and engages slot 162 of safety cage 156. With the safety slide 154 in the full distal position, the pin 158 forces safety cage 156 such that leg 164 is forced into a slot 166 in pusher 170 that locks the movable pusher 170 against distal movement. In this position, safety slide 154 covers the word "READY" (or any other word, mark or appropriate indicia) and exposes the word "SAFE" (or any other word, mark or appropriate indicia) embossed on handle half 312. In this position, the safety latch 152 prevents the automatic mechanism 150 from premature firing during shipment or handling. With safety slide 154 in the proximal-most position, the pin 158 forces safety slide 154 to the right, thus removing leg 164 from the slot 166 in pusher 170. In this position the automatic mechanism 150 is free to initiate when first sealing element 320 interacts with the inside of a vessel wall. In this configuration safety slide 154 covers the word "SAFE" and exposes the word "READY" on handle half 312.

Flexible pusher rod 316 is a cannulated cylinder, the proximal end of which is connected by an adhesive or by another appropriate method to the movable pusher 170. The movable pusher 170 has a front portion 172 with an opening 174 for engagement with the flexible pusher rod 16 and to allow the flexible shaft 218 to pass through front portion 172. The pusher 170 also has a rear portion 176 that is divided into an upper portion 176a and a lower portion 176b, the upper portion 176a and a lower portion 176b defining an opening 178 therebetween.

The automatic mechanism 150 also includes a shaft retaining element 180 that, in the initial or preactivation stage, is disposed in opening 178 defined by the upper portion 176a and a lower portion 176b of pusher 170. The shaft retaining element 180 also has an opening 182 passing therethrough to allow the flexible shaft 318 to pass there-through and extend proximally in the automatic mechanism 150. However, the flexible shaft 318 is fixedly attached to the shaft retaining element 180. The flexible shaft 318 therefore extends almost the entire length of the device 300. As noted above, the flexible shaft 318 is also connected to the knobbed rigid shaft 326 of the seal assembly 320. A tensile force on the flexible shaft 318 causes the automatic mechanism 150 to fire.

The automatic mechanism 150 also has a spring 190, which is illustrated as a cylindrical spring, but could be any resilient element and have any configuration. The spring 190 engages, at its proximal end, the proximal end of the handle 312,314. The spring 190 is disposed around a spring retainer 194 and engages at its distal end, the front end 196 of the spring retainer 194. The spring 190 is biased against the front end 196 of the spring retainer 194 to push the spring retainer 194 against the pusher 170, as described in more detail below.

The automatic mechanism 150 also has two retention elements 200 that are rotatably mounted in the housing 312,314. The two retention elements 200 are illustrated as being generally triangular, but could be of any shape or configuration as long as they perform the functions noted below. The retention elements 200 are disposed to engage the front end 196 of the spring retainer 194 and the shaft retaining element 180. In fact, each of the two retention elements 200 engage a notch 202 on either side of the shaft retaining element 180. The retention elements 200 each have an end portion 204, preferably a flat surface, that engages an internal surface of the notches 202. The retention elements 200 are disposed on round projections 206 extending upward from the handle 314. The projections 206 could also project downward from the handle 312.

With regard to the use of the device 300, the disclosure of the use of the device is discussed in detail in the co-pending Ser. No. 13/746,276, the content of which is incorporated herein by reference and summarized again below.

The automatic mechanism is coupled to the seal assembly 320 by a flexible pusher 316 and a flexible shaft 318, as in the prior embodiment. Seal assembly 320 has a first sealing element 322, a flexible member 324, a knobbed rigid shaft 326, an outer floating element 328, and a second sealing element 330. Knobbed, rigid shaft 326 has a proximal section 332 and a distal section 334 separated by a weakened notch feature 336, which is configured to separate seal assembly 320 from the rest of the closure device 300 once the automatic deployment and sealing process is complete. The length of the distal section 334 of knobbed shaft 326 is dictated by the thickness of the vessel wall that can be accommodated. The first sealing element 322 also has a distal section 340 configured to, with the assistance of the flexible member 324, interface with the inside wall of a vessel to be sealed; a knobbed, rigid distal shaft section 334 (which is a part of the knobbed, rigid shaft 326); and ankle section 342 joining the distal section 340 to the knobbed, rigid distal shaft section 334. The ankle section 342 is attached to distal section 340 at an angle α, which is preferably at an angle of about 45°. See FIG. 18. Although other angles may be used, the value of angle α may cause other values of the seal assembly to be changed. Applicant also notes the that the first sealing element 322 is formed with the distal section 340, ankle section 342, and the knobbed, rigid shaft 326 at the same time and from the same material. As such, the first sealing element 322 is an inte-grally formed element and the distal section 340 is not designed to move relative to the knobbed, rigid distal shaft section 334 at any time, except through deformity. As indicated in the parent patent, the first sealing element is preferably a one single-piece component.

A more detailed view of the first sealing element 322 and the knobbed rigid shaft 326 is presented in FIGS. 16A-21. The first sealing element 322 has the distal section 340, ankle section 342 and the knobbed, rigid distal shaft section 334. The distal section 340 has a proximal or top surface 350, a bottom surface 352 and a heel 356. The top surface 350 can be of any configuration (e.g., flat, convex, etc) and still come within the scope of the present invention. The bottom surface 352 is preferably flat, but may have other configurations as well. The heel 356 preferably has a greater thickness than the remainder of the distal section 340 and, as discussed below is disposed into a cavity in the inserter. The distal section 340 has a thickness that increases from the front (or distal) end 358 to the rear (or proximal) end 360. In the embodiment illustrated in the figures, the thickness increases from 0.28 mm at the front end 358 to 0.30 mm at the rear end 360. However, other thicknesses and tapered shapes fall within the scope of the present invention.

Figure 16A:
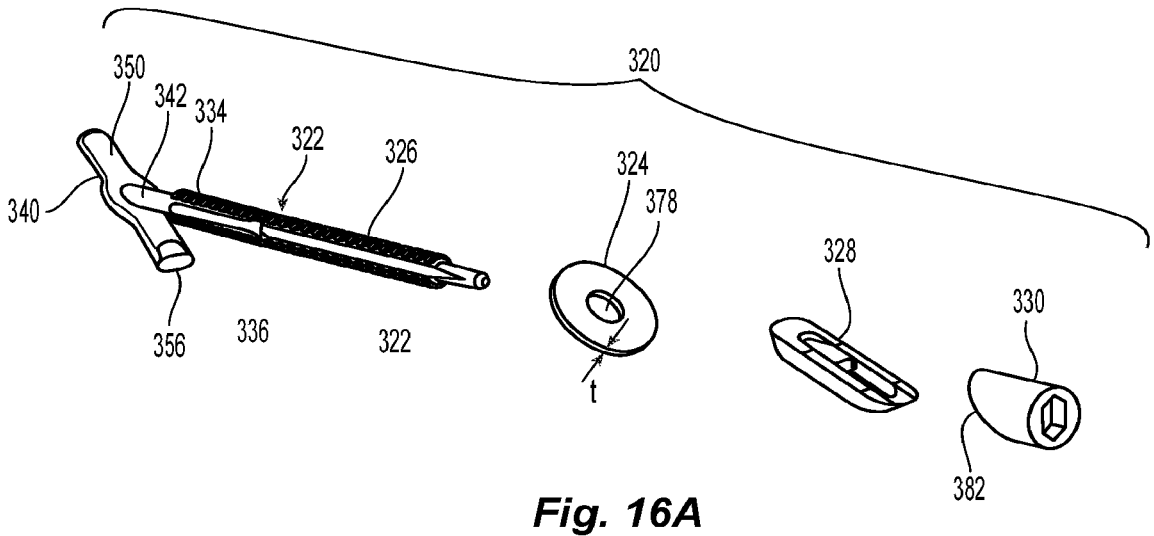
FIG. 16A is an exploded, perspective view of the first sealing element and the shaft.
Figure 16B:
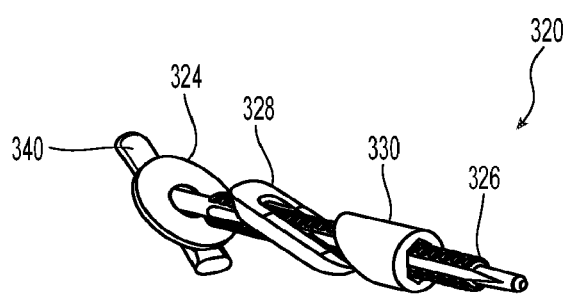
FIG. 16B is a perspective view of the first sealing element and the shaft of FIG. 16A in an assembled state.
Figure 16C:
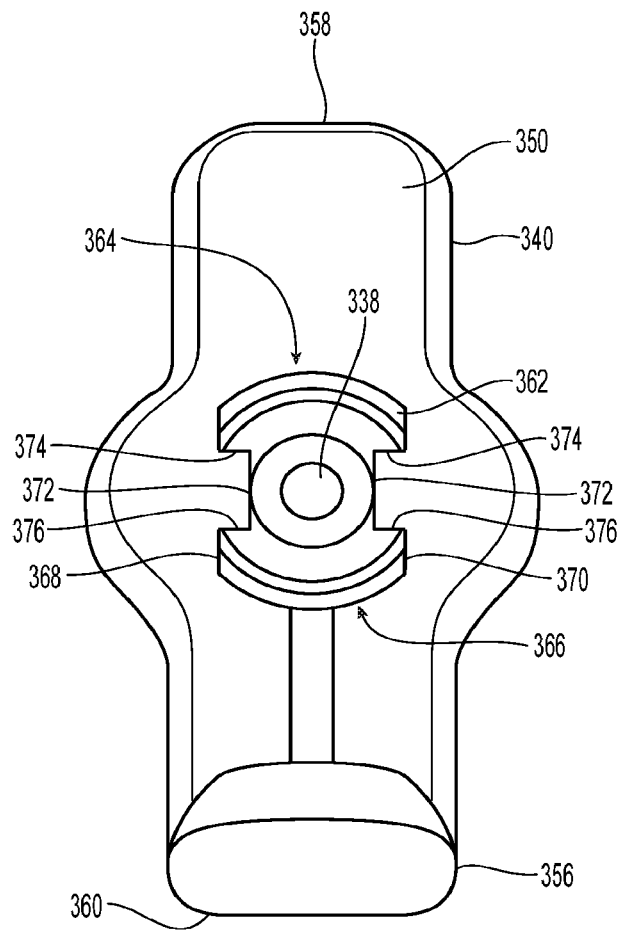
FIG. 16C is a top view of the first sealing element and shaft looking down the shaft.

A top view of the knobbed, rigid shaft 326 and the first sealing element 322 is illustrated in FIG. 16C. The knobbed, rigid shaft 326 has a proximal end 338 that may be con-nected to the flexible shaft 318 in any appropriate fashion, e.g., glued, soldered, press-fit, friction fit, etc. Alternatively, the flexible shaft 318 may also be integral with the knobbed, rigid shaft 326, i.e., be formed at the same time with the same material making it an "integral" piece. The knobbed, rigid shaft 326 has knobs 362 along the upper surface 364 and the lower surface 366. The knobbed, rigid shaft 326 also has opposite sides 368,370, each side of which includes a groove 372 that runs along the length of the knobbed, rigid shaft 326 between the ankle section 342 and the proximal end 338. The grooves 372 are preferably rectangular (or square) in cross section for reasons that will become appar-ent below. As such each of the grooves 372 have a front (or first) surface 374 and a rear (or second) surface 376. It is noted that the front surface 374 faces the rear portion of the knobbed, rigid shaft 326, while the rear surface 376 faces the front of the knobbed, rigid shaft 326. The grooves 372 cooperate with the other portions of the seal assembly 320 to ensure that the outer floating element 328 and the second sealing element 330 are properly positioned, as discussed in more detail below. Since the grooves 372 are smaller than the sides 368,370, the sides 368,370 present a flat surface for the outer floating element 328, discussed below.

Figure 20:
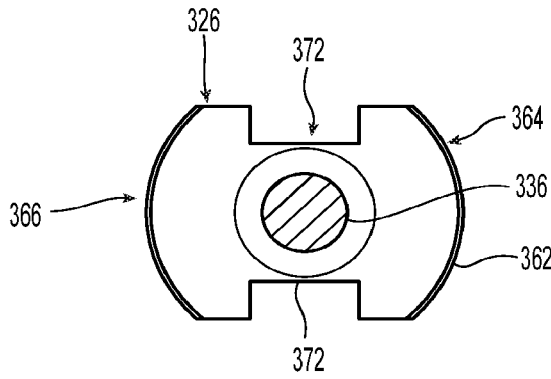
FIG. 20 is a cross section view of the shaft at the location of the reduced portion.
Figure 21:
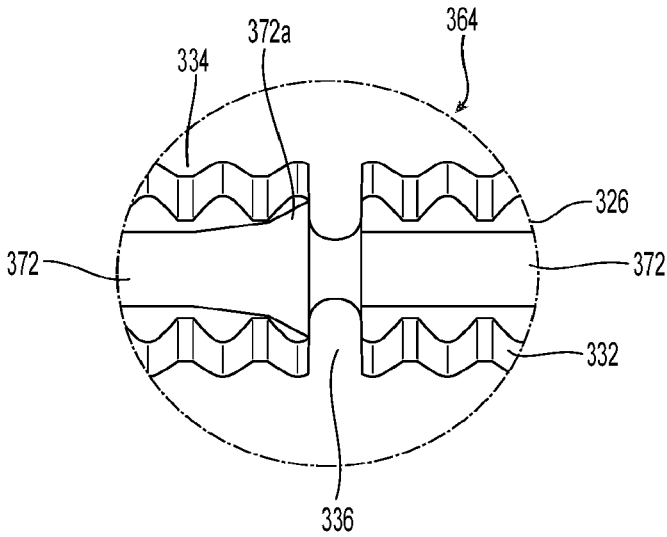
FIG. 21 is a partial side view of the shaft at the location of the reduced portion

Illustrated in FIGS. 20 and 21 is a cross section of the knobbed, rigid shaft 326 at the weakened notch feature 336. The weakened notch feature 336 has a smaller cross section than any other portion of the knobbed rigid shaft 326. This allows for the knobbed, rigid shaft 326 to be broken at this point upon activation of the insertion device 300 by exerting a force in the direction of the length of the knobbed, rigid shaft 326, causing the knobbed, rigid shaft 326 to break at the weakened notch feature 336. In order to prevent the weakened notch feature 336 from breaking prematurely, a c-shaped ring may be clipped into the weakened notch feature 336 as noted above. The width of notch feature 336 is sized to equal the space between knobs 362 so that second seal 328 can easily transition over notch feature 336 upon automatic activation of device 300. The c-shaped ring prevents the knobbed, rigid shaft 326 from being tilted off center and breaking prematurely.

In FIG. 21, the groove 372 in the knobbed, rigid distal shaft section 334 preferably flares outward at 372a at the weakened notch feature 336, to ensure that the outer floating element 328 and its components float over the the weakened notch feature 336 during operation without skiving on a portion of the groove 372 at that location.

Figure 17:
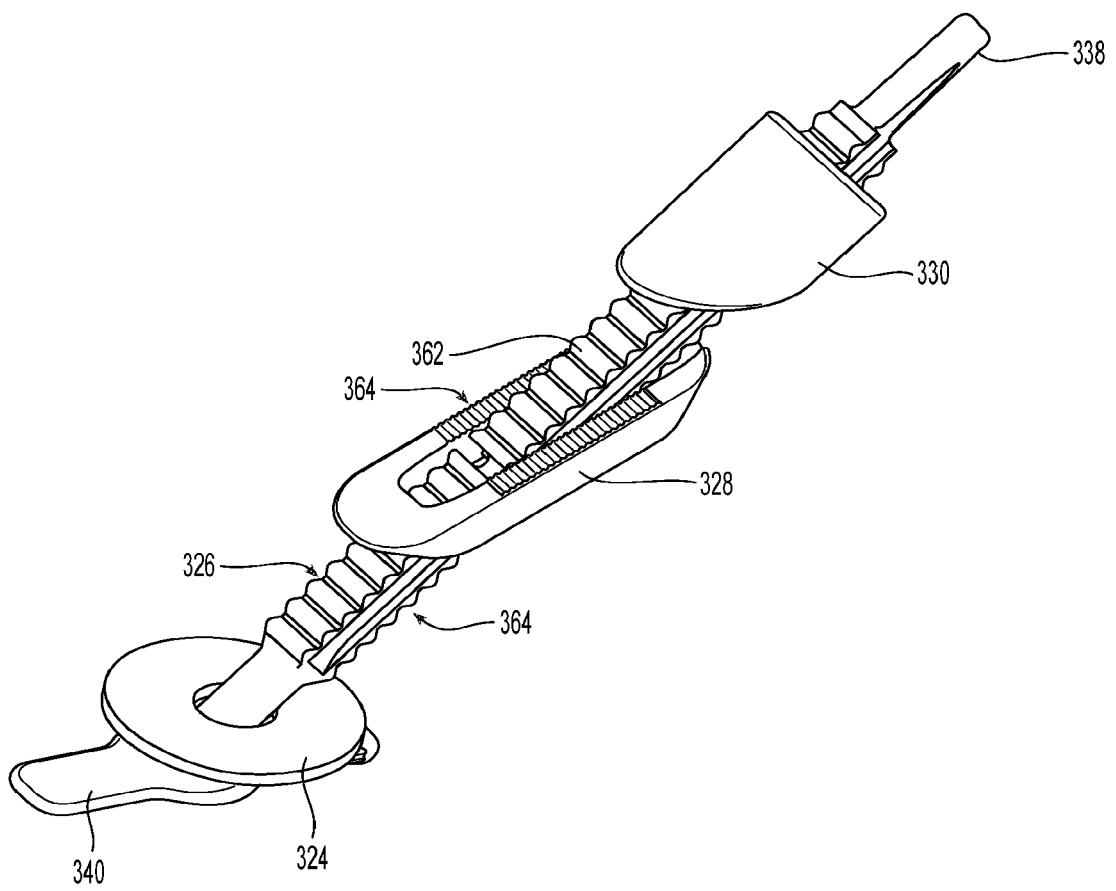
FIG. 17 is a perspective view of the seal assembly of FIG. 15.
Figure 18:
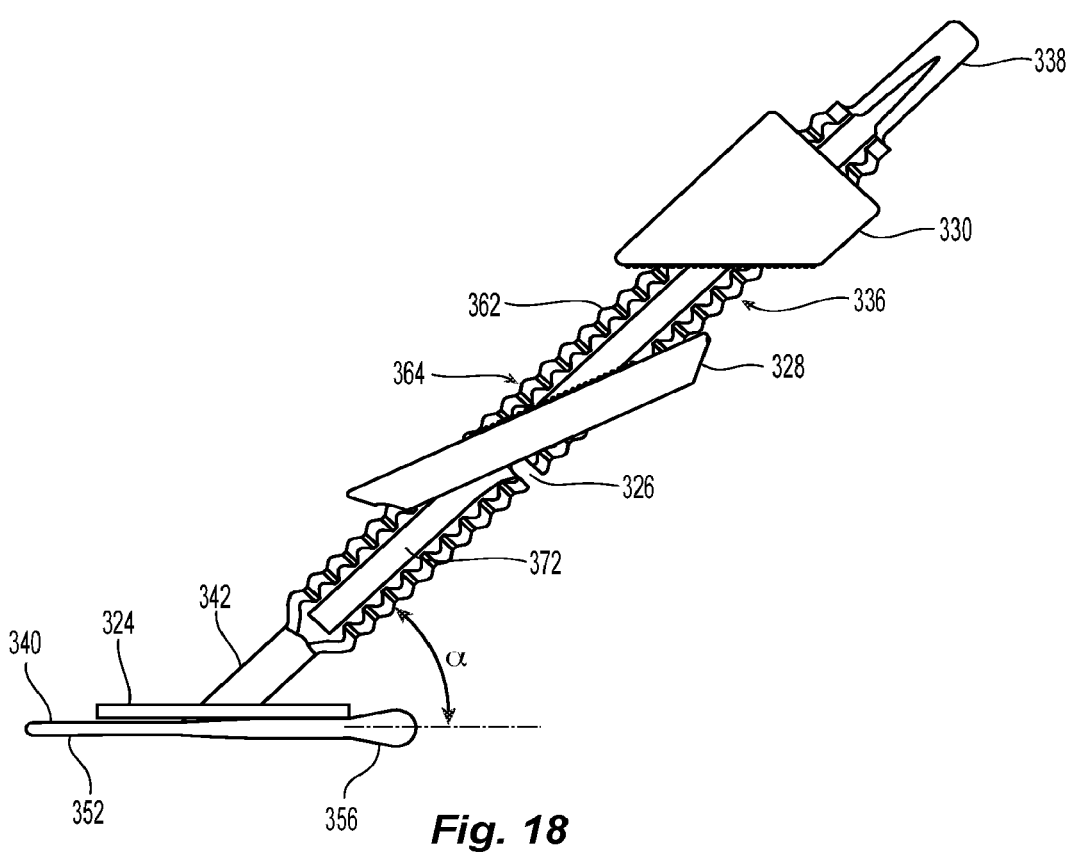
FIG. 18 is a side view of the of the seal assembly of FIG. 15.
Figure 19:
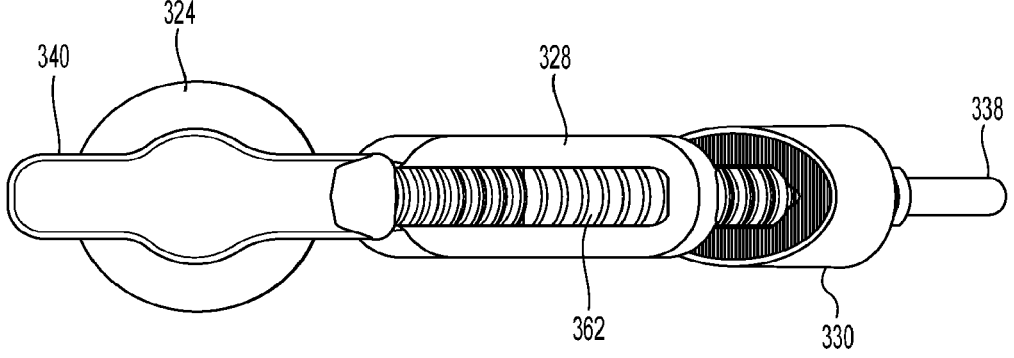
FIG. 19 is is a bottom view of the of the seal assembly of FIG. 15.

The flexible member 324, along with distal section 340, assists in sealing the opening in the vessel wall. The flexible member 324 is illustrated as being a circular member having an opening 378 in a middle portion thereof. The flexible member 324 has a thickness t, which is preferably around 0.2 millimeters. Since the flexible member 324 is preferably made from 70% L-lactide 30% caprolactone copolymer, it is able to being deformed as described below. As illustrated in FIGS. 16B and 17, the flexible member 324 is disposed around the ankle portion 342 and against the top surface 350 of the distal section 340. Preferably, the flexible member 324 is attached to the top surface 350 of the distal section 340. It can be attached in any number of ways, including heat-staking or welding the flexible member 324 to the top surface 350, using an approved adhesive between the flexible member 324 and the top surface 350 flexible member 324. Alternatively, the opening 378 could be slightly smaller than the diameter of the ankle portion 342, preventing the flexible member 324 from moving along the length of the knobbed, rigid shaft 326 at the ankle portion 342. As explained in more detail below, the flexible member 324 is disposed between the distal section 340 and the inner wall of the vessel. See, e.g., FIG. 30.

While the opening 378 is a contained opening, it is also possible that there be a slit (or small path) from the outside of the flexible member 324 allowing the flexible member to be disposed around the ankle portion 342 without having to slide it the length of the knobbed, rigid shaft 326.

Figure 22A:
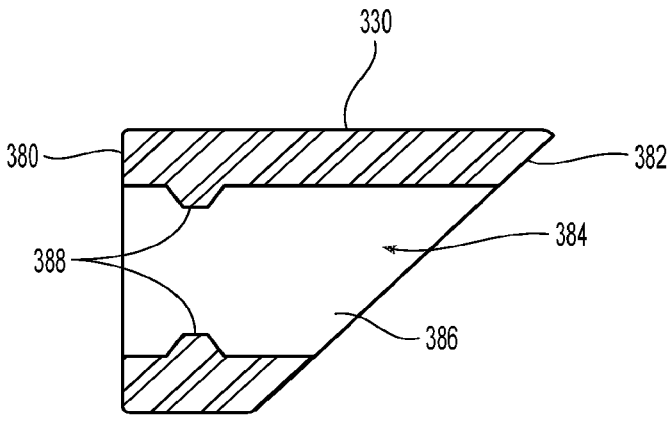
FIG. 22A is a cross section view along a longitudinal axis of a second sealing element of the seal assembly of FIG. 16.
Figure 22B:
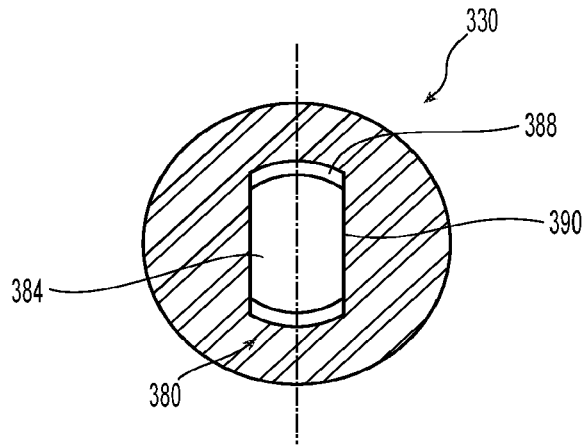
FIG. 22B is a cross section view of the second sealing element of the seal assembly of FIG. 16 that is orthogonal to the view in FIG. 24A.
Figure 23A:
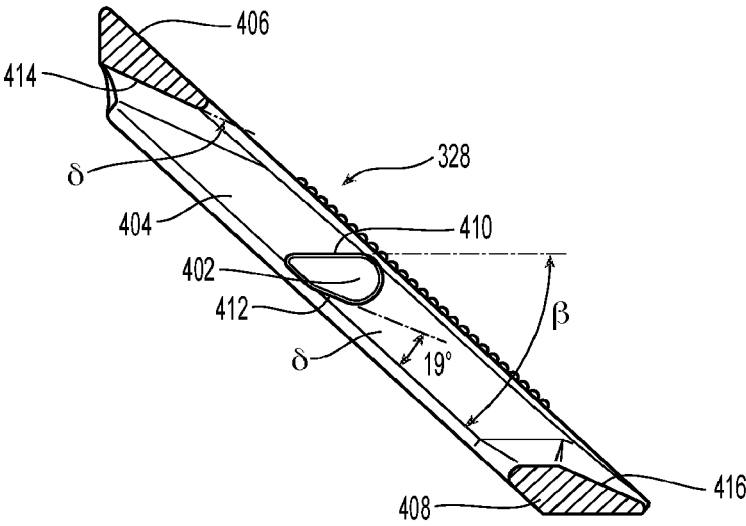
FIG. 23A is a side view of a cross section of another embodiment of an outer floating member.
Figure 23B:
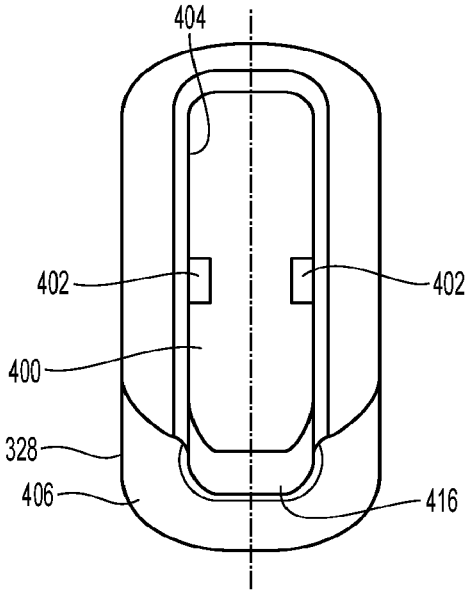
FIG. 23B is a top view of the outer floating member of FIG. 22A.

Second sealing element 330 is shown in more detail in FIGS. 22A and 22B. The second sealing element 330 has a proximally facing surface 380 and a sloped distally facing surface 382. An internal opening 384 defined by the internal surface 386 extends between the proximally facing surface 380 and the sloped distally facing surface 382. The internal surface 386 has extending therefrom and into the internal opening 384 projections 388 that interface with and engage the knobs 362 with an interference fit such that second sealing element 330 and knobbed, rigid shaft 326 function as a one way latch assuring an adequate compression force regardless of the blood vessel wall thickness.

Referring to FIG. 22B, the internal opening 384 of second sealing element 330 have two flat surfaces 390 on opposite sides of the internal opening 384 that interface with flat surfaces 368,370 of knobbed rigid shaft 326 to provide rotational stability of the seal assembly components 328, 330, thus assuring that the sloped distally facing surface 382 and the fully deployed outer floating foot 328 remain parallel with the distal section 340 of the first sealing element 322 and the proximal or top surface 350 in particular.

The outer floating element 328 is illustrated in detail in FIGS. 23A-24B. The outer floating element 328 is generally rectangularly shaped and has a rectangularly shaped central aperture 400 and two protrusions 402 that extend from the longest side walls 404 into the aperture 400. The outer floating element 328 has a top surface 406 and a bottom surface 408, which are generally parallel to one another. The protrusions 402 are configured to engage and allow the outer floating element 328 to travel along the knobbed, rigid shaft 326 in the grooves 372. The protrusions are somewhat tear drop shaped, but have two flat surfaces, a first flat surface 410 and a second flat surface 412. The outer floating element 328 also has two inclined surfaces 414 and 416, one at either end of the outer floating element 328 and defines the ends of the aperture 400. The first flat surface 410 is at an angle ß relative to the top and bottom surfaces 406,408 of outer floating element 328. See FIG. 23A. Preferably angle ß is about a 45 degree angle but could be anywhere between 35 and 55 degrees and still fall within the scope of the present invention. The second flat surface 412 makes an angle γ relative to the top and bottom surfaces 406,408. See FIG. 23A. Preferably angle γ is about a 19 degree angle but could be anywhere between 15 and 25 degrees and still fall within the scope of the present invention. As would be obvious, the two inclined surfaces 414 and 416 are also parallel to the second flat surface 412 as will be explained below.

Figure 24A:
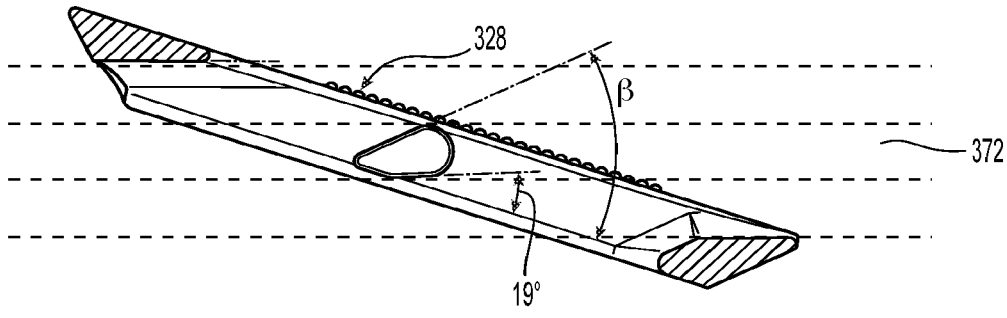
FIG. 24A is a side view of cross section view of the outer floating member in FIG. 22A in a first position relative to the shaft.
Figure 24B:
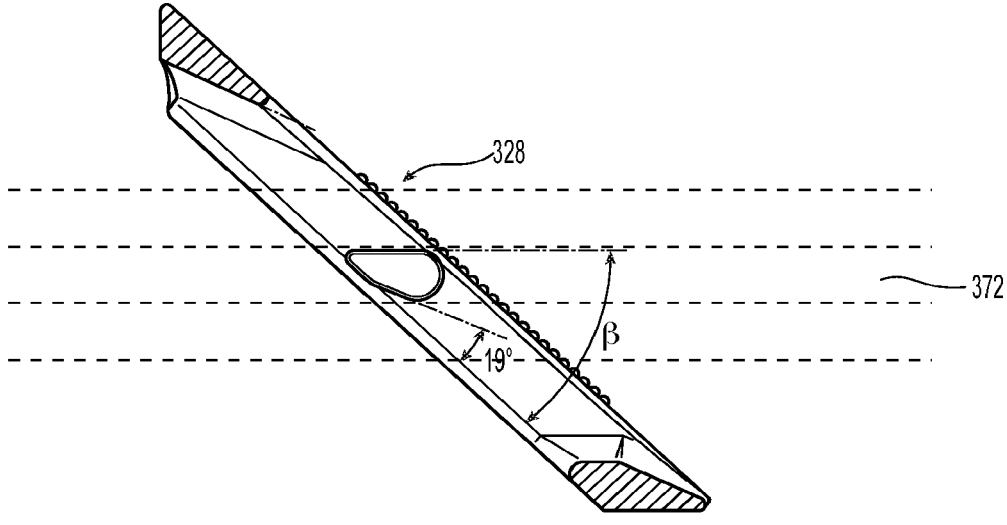
FIG. 24B is a side view of cross section view of the outer floating member in FIG. 22A in a second position relative to the shaft.

Turning to FIGS. 24A and 24B, the positioning of the outer floating element 328 will be explained. In both figures, the dotted lines correspond to the surfaces of the knobbed, rigid shaft 326 presented to the outer floating element 328. In particular, the two middle lines correspond to the front (or first) surface 374 and the rear (or second) surface 376 of the groove 372. Thus, the two protrusions 402 will slide along between those two middle lines. The two outside lines correspond to the upper 364 surface and the lower 366 surface of the outer floating element 328. In FIG. 24A, the outer floating element 328 is illustrated in its stored version—to be inserted into, or already in the inserter. Thus, in the position of FIG. 24A, the outer floating element 328 has, relative to the rest of the seal assembly 320, the smallest profile and will allow it to pass through a smaller cannula.

FIG. 24B illustrates the outer floating element 328 relative to the knobbed, rigid shaft 326 after it exits the cannula. That is, the outer floating element 328 has been engaged by the second sealing element 330 (not shown in the figures) and because the size of the projections 402 relative to the groove 372, the outer floating element 328 can rotate (clockwise in FIG. 24B) relative to the knobbed, rigid shaft 326 to be in a position to engage the outside of the vessel. See, e.g., FIGS. 30 and 31.

Figure 25:
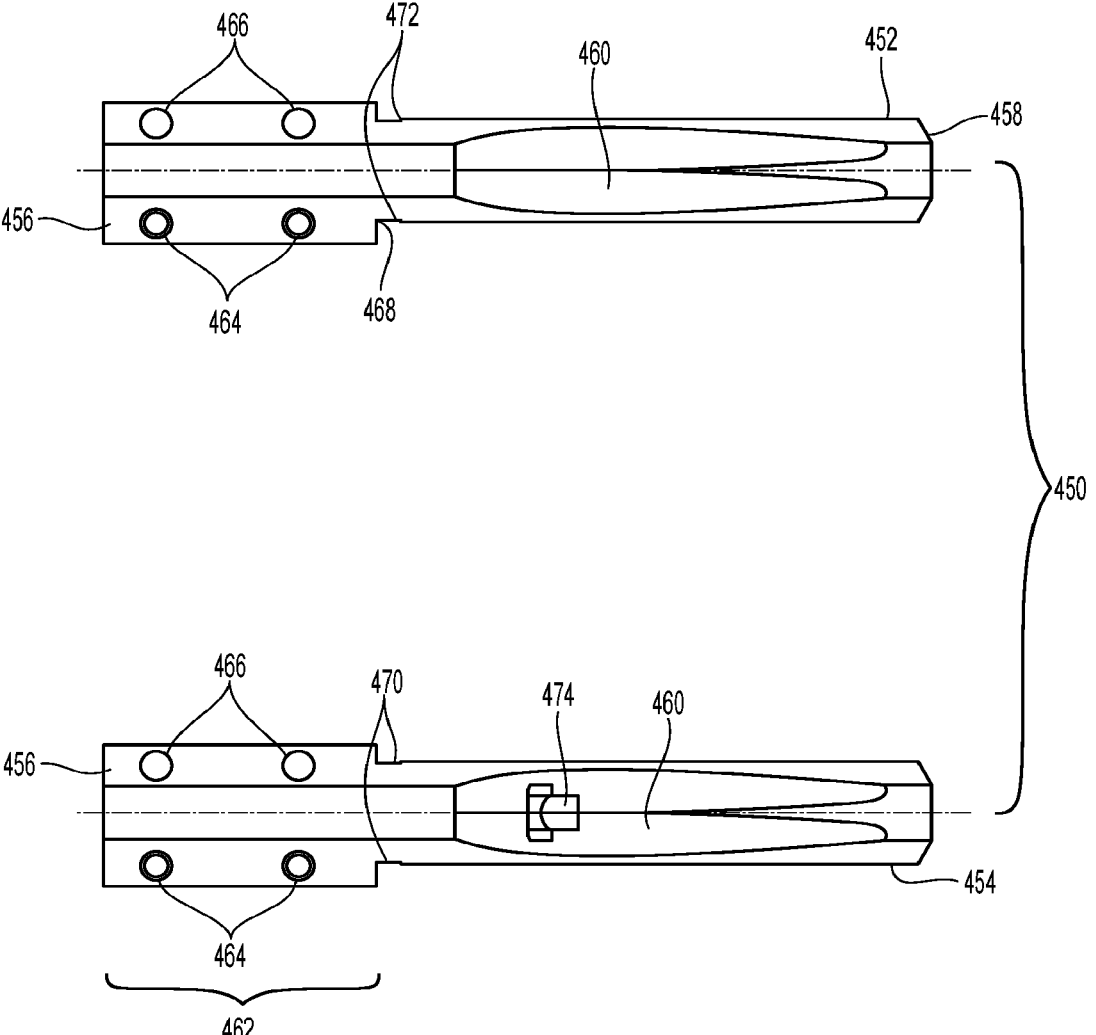
FIG. 25 is an exploded, perspective view of the sheath introducer for use with the seal assembly of FIG. 16.
Figures 26, 27:
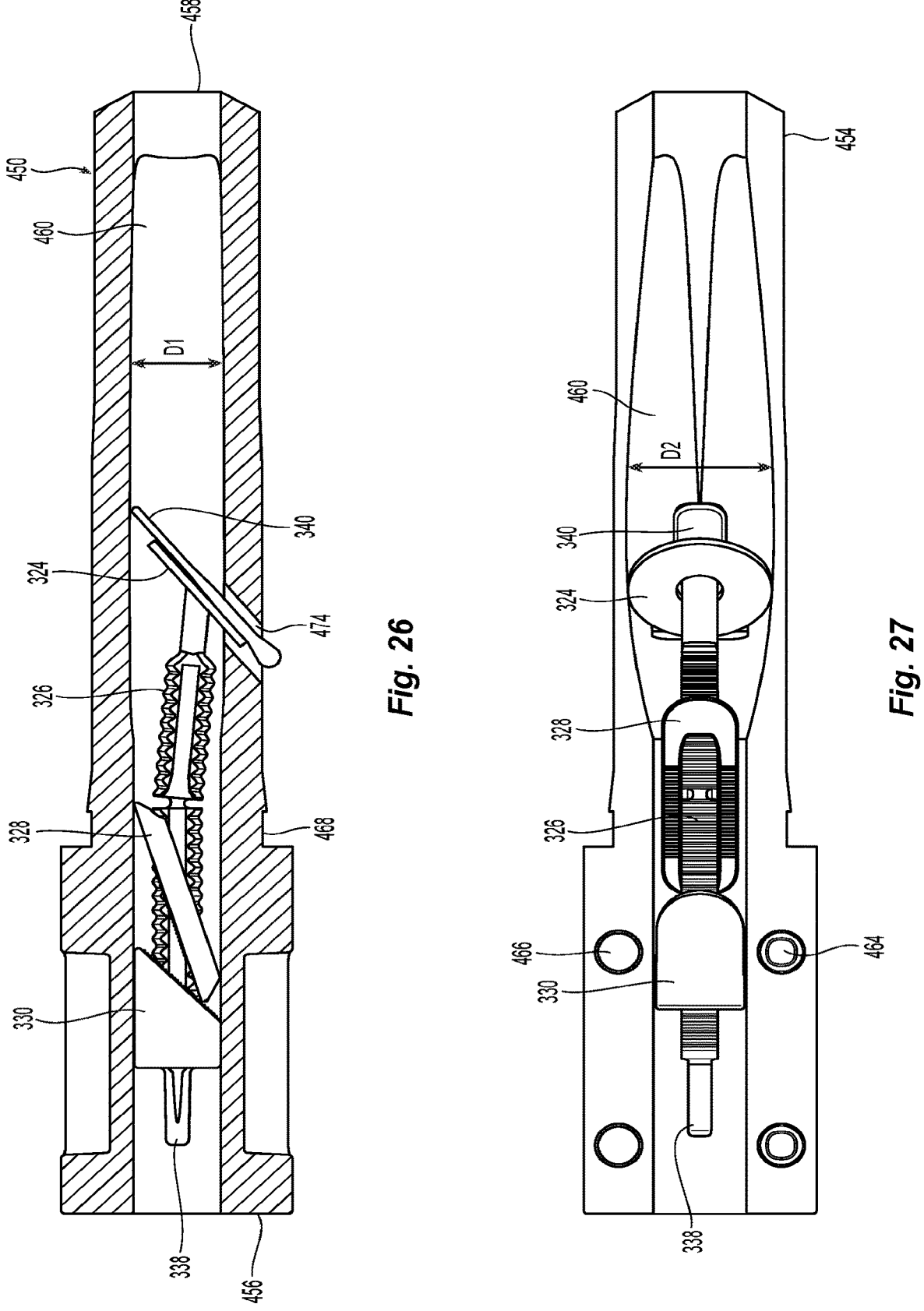
FIG. 26 is a cross section view of the seal assembly constrained in the inserter of FIG. 26.
FIG. 27 is a top view of the seal assembly in the bottom portion of the inserter.
Figure 28:
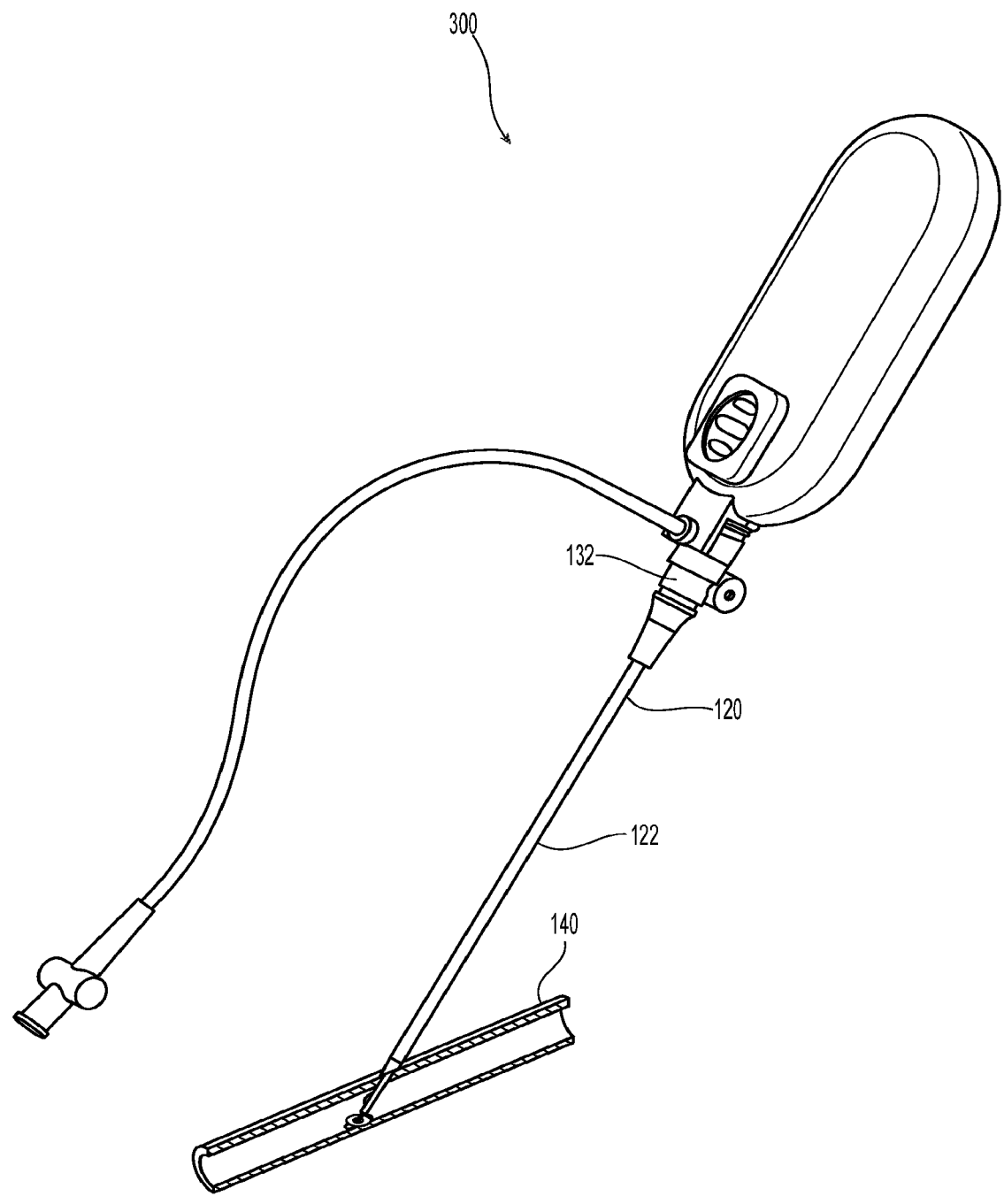
FIG. 28 is a perspective view of the sealing device inserted into a blood vessel.
Figure 29:
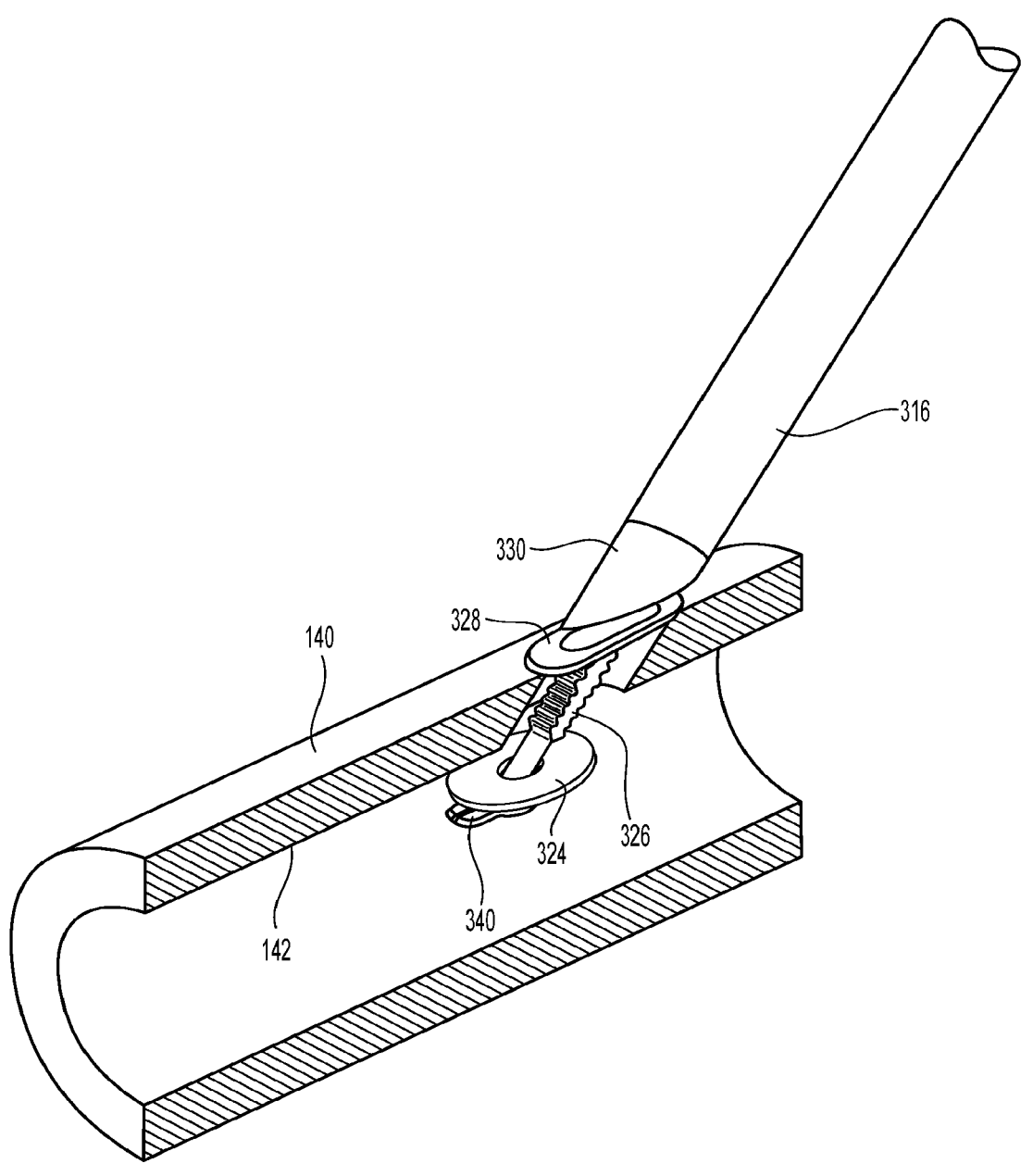
FIG. 29 is partial cross section view of a vessel with the sealing device inserted therein.
Figure 30:
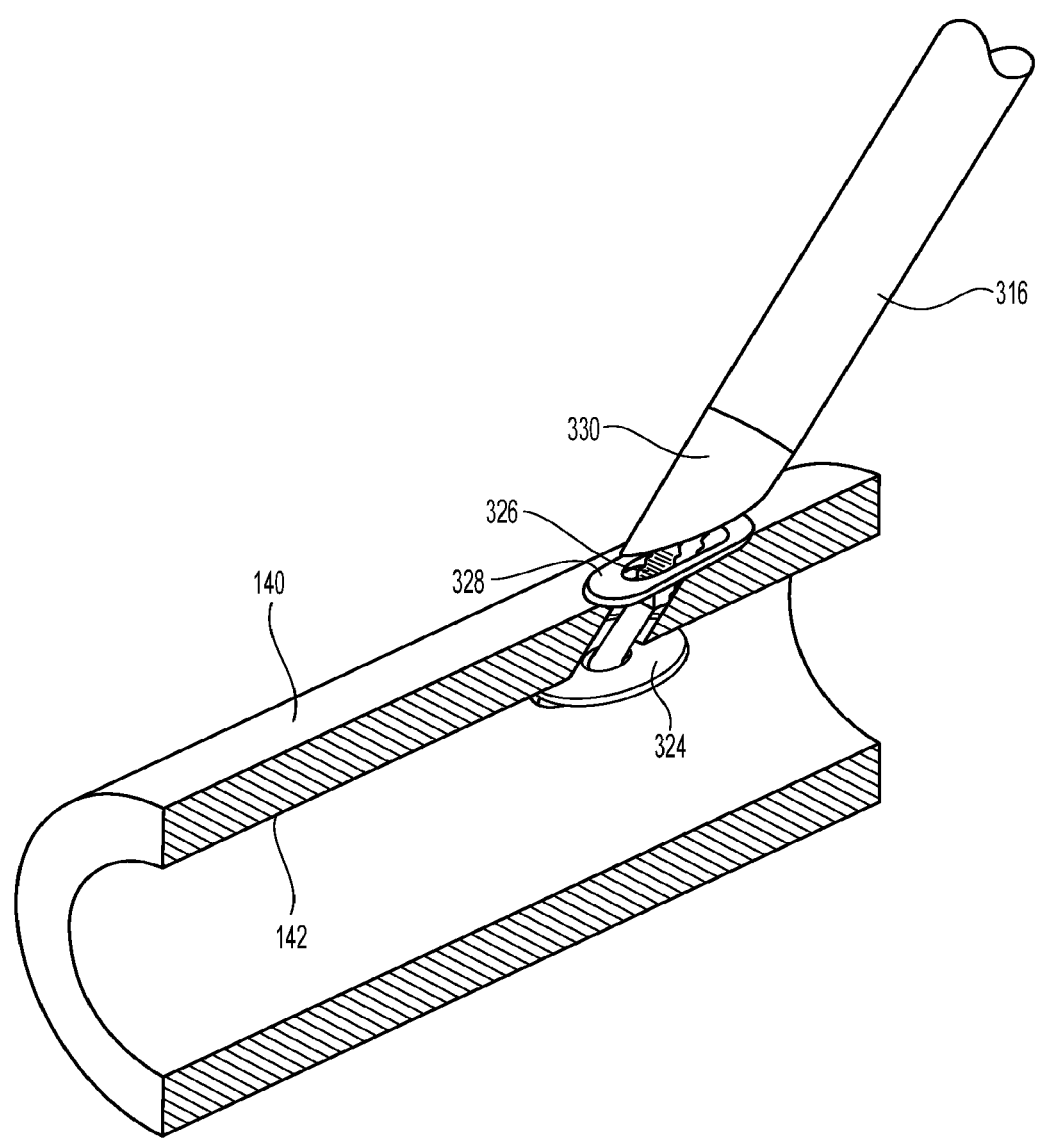
FIG. 30 is perspective view of the sealing device inserted into the blood vessel just before the sealing device is activated.

An inserter 450 is illustrated in FIGS. 25-27. The embodiment of the inserter 450 illustrated has a first portion 452 and a second portion 454, which are illustrated as a top half and a bottom half. Naturally, the portions 452,454 could have other names (e.g., side portions) and still fall within the scope of the present invention. The inserter 450 has a proximal end 456 and a distal end 458. When the portions 452,454 are assembled, a longitudinal opening 460 is created that extends through the inserter 450. The inserter 450 preferably has at the proximal end 456 a proximal section 462 that has a constant diameter outer surface and a constant diameter for the longitudinal opening 460 at the proximal section 462. The proximal section 462 of each of the portions 452,454 has a a number of projections 464 and openings 466. The projections 464 of one portion 452,454 correspond to the openings 466 of the other portion 452,454, thereby allowing the two portions 452,454 to be brought together and aligned for use. Forward of the proximal section 462 is a reduced diameter area 468, which then increases in diameter at 470 creating a shoulder 472 before tapering back down to a smaller outer diameter at the distal end 458.

The longitudinal opening 460 in inserter 450 allows for the seal assembly 320 to be loaded therein, sterilized, stored, and then used by a doctor. Typically, if a seal assembly is contained within a confined space and then sterilized, the sterilization causes the seal assembly to maintain the configuration in which it is sterilized. Even if the material normally was some shape memory (allowing the material to spring back to its original shape or configuration), the sterilization has been found by the inventor to prevent the materials from returning to their original configuration. Thus, the current inserter 450 allows for the seal assembly 320 to be loaded without any real change in configuration. The longitudinal opening 460 has been designed to hold the first sealing element 322, a flexible member 324, a knobbed rigid shaft 326, an outer floating element 328, and a second sealing element 330 without this issue. To do so, however, the portion 454 has an aperture 474 to allow for the heel 356 of the distal section 340 to be disposed therein. While the aperture 474 is illustrated as extending through the portion 454, it is possible that there only be a depression, groove, or dimple that does not penetrate all the way through the portion 454.

Turning to FIG. 26, a cross section of the inserter 450 with the seal assembly 320 disposed therein illustrates the position of the seal assembly 320 within the inserter 450. As should be clear, the cross section is through the center of both portions 452,454. It should also be noted that the distance D1 of between the two portions 452,454 of the longitudinal opening 460 is generally constant. The position of the outer floating element 328 relative to the knobbed, rigid shaft 326 and the position of the flexible member 324 relative to the distal section 340 allow the inserter to have a minimum size.

FIG. 27 illustrates the the seal assembly 320 within the inserter 450 from above the inserter 450. In this view, it is clear that the diameter D2 of the longitudinal opening 460 is larger in the horizontal plane; allowing the flexible member 324 to hold its original configuration. The longitudinal opening 460 at the proximal section 462 is also sized to allow the outer floating element 328 and the second sealing element 330 to pass therethrough. The longitudinal opening 460 at the distal end 458 is smaller than the diameter D2, but the flexible member 324 and the distal section 340 can be deformed and then return to their to original shape for use in the patient.

A method of using the current invention in conjunction with FIGS. 28-31 is as follows: The device 300, and in particular the seal assembly 320 is inserted into inserter 450 that surrounds seal assembly 320 such that seal assembly 320 can pass through sheath valve 132 and to the sheath 120. This allows for the simultaneous removal of the device 300 and the sheath 120, if the sheath is not removed prior to the activation of the automatic mechanism. Inserting pusher 316 through sheath 120, including valve 132 and cannula 122, causes at least a portion of seal assembly 320 to exit the distal end of cannula 122 and into blood vessel 140. See FIG. 29. The sheath 120 may then be removed from the device 300. Pulling on the closure device 300, the flexible member 324 and the distal portion 340 of first sealing element 322 engages the interior blood vessel wall 142. See FIG. 30. This would also remove the second sealing element 330, the outer floating element 328, and the pusher 316 from within the blood vessel 140. Continuing to pull on the sealing assembly 320, and therefore flexible shaft 318, triggers the automatic mechanism 150 in the closure device 300, which pushes pusher 316, and which in turn pushes second sealing element 330, and the outer floating element

Figure 31:
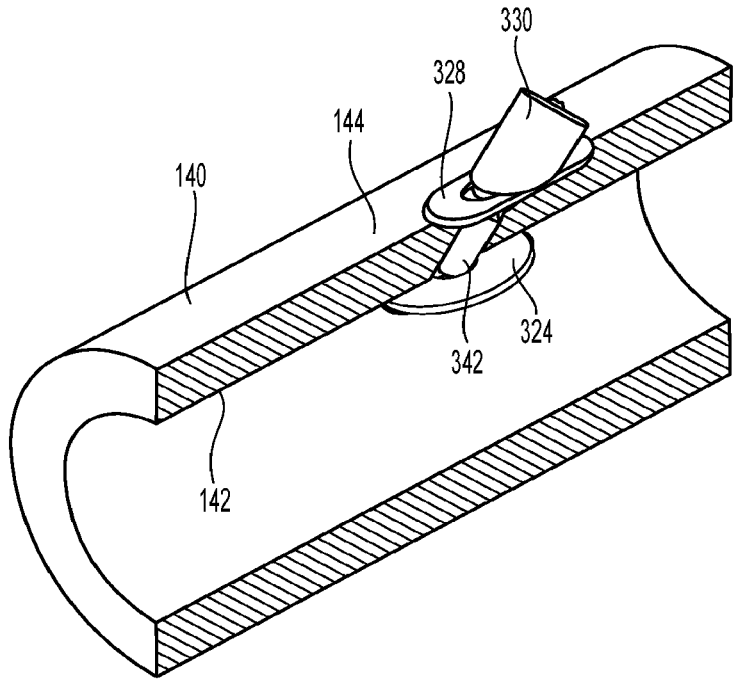
FIG. 31 is a perspective view of the seal assembly blocking the opening in the blood vessel after activation of the sealing device.

328 distally such that the outer floating element 328 is in contact with outer wall of blood vessel 140. This will sandwich the outer floating element 328, the blood vessel 140 and the flexible member 324 between the first and second sealing elements 322, 330 such that the opening in blood vessel 140 is hemostatically sealed, as shown in FIG. 31.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A seal assembly for sealing an opening in the wall of a blood vessel, the blood vessel having an interior wall surface, exterior wall surface, and a lumen, the seal assembly comprising:

a first sealing element for placing inside the lumen of the blood vessel;

a shaft having a rigid formation with the first sealing element and in a same predetermined configuration relative to the first sealing element before and after insertion of the first sealing element into the lumen, the shaft having a length sufficient to extend through the opening of the blood vessel and at least a portion of any overlying tissue;

an outer floating element slidingly movable along the shaft, the outer floating element having a top surface and a bottom surface; and a second sealing element, the second sealing element slidingly movable relative to the first sealing element along the shaft to engage the outer floating element and configured to position the bottom surface of the outer floating element against the exterior wall surface of the blood vessel to seal the opening in the blood vessel, wherein the shaft has at least two sides, the at least two sides each having a groove along a portion thereof and the outer floating element has an aperture to receive the shaft therethrough, the aperture generally being rectangular and having two protrusions extending into the aperture and configured to extend into the groove on a respective side of the shaft.

2. The seal assembly for sealing an opening in the wall of a blood vessel according to claim 1, wherein the shaft has four sides, two of the four sides having a plurality of equally spaced projections along a length thereof.

3. The seal assembly for sealing an opening in the wall of a blood vessel according to claim 1, wherein each of the two protrusions has a first surface capable of engaging a first wall of the groove and a second surface capable of engaging a second wall of the groove.

4. The seal assembly for sealing an opening in the wall of a blood vessel according to claim 3, wherein when the first surface engages the first wall of the groove, the bottom surface of the outer floating element is disposed relative to the first wall at a first angle of between 35 and 55 degrees.

5. The seal assembly for sealing an opening in the wall of a blood vessel according to claim 4, wherein the first angle is 45 degrees.

6. The seal assembly for sealing an opening in the wall of a blood vessel according to claim 3, wherein when the second surface engages the second wall of the groove, the second wall facing the first wall across the groove, and the bottom surface of the outer floating element is disposed relative to the second wall at a second angle of between 15 and 25 degrees.

7. The seal assembly for sealing an opening in the wall of a blood vessel according to claim 6, wherein the second angle is 19 degrees.

8. The seal assembly for sealing an opening in the wall of a blood vessel according to claim 1, wherein the shaft has a reduced portion, the reduced portion having a cross section being smaller than a cross section of any other portion of the shaft.

9. The seal assembly for sealing an opening in the wall of a blood vessel according to claim 1, further comprising an inserter, the inserter comprising a housing have a first portion and a second portion, the first portion and second portion having a proximal end and a distal end;

a longitudinal opening extending through the housing when the first and second portion are connected to one another and opening at the proximal and distal ends;

an aperture in one of the first and second portions, the aperture configured to receive a portion of the first sealing element when the first and second portion are connected to one another and the seal assembly is inserted therein.

10. The seal assembly for sealing an opening in the wall of a blood vessel according to claim 9, wherein the longitudinal opening has a first opening portion and a second opening portion, the first opening portion having a constant diameter and the second opening portion has a variable diameter.

11. The seal assembly for sealing an opening in the wall of a blood vessel according to claim 10, wherein the aperture is disposed in the inserter at the second opening portion.

12. The seal assembly for sealing an opening in the wall of a blood vessel according to claim 9, where in the bottom surface of the outer floating member is disposed relative to the shaft at an angle of between 15 and 25 degrees.

13. The seal assembly for sealing an opening in the wall of a blood vessel according to claim 9, the inserter has an outer surface, the outer surface having a first outer diameter at the distal end thereof and a second diameter between the distal and proximal ends, the second diameter being larger than the first diameter.

14. A seal assembly for sealing an opening in the wall of a blood vessel, the blood vessel having an interior wall surface, exterior wall surface, and a lumen, the seal assembly comprising:

a first sealing element for placing inside the lumen of the blood vessel;

a shaft having a rigid formation with the first sealing element and in a same predetermined configuration relative to the first sealing element before and after insertion of the first sealing element into the lumen, the shaft having a length sufficient to extend through the opening of the blood vessel and at least a portion of any overlying tissue, and the shaft and the first sealing element are a single one-piece component;

a flexible member surrounding at least a portion of the shaft adjacent the first sealing element; and a second sealing element, the second sealing element slidingly movable relative to the first sealing element along the shaft and configured to seal the opening in the blood vessel, wherein the shaft has at least two sides, the at least two sides each having a groove along a portion thereof and the outer floating element has an aperture to receive the shaft therethrough, the aperture generally being rectangular and having two protrusions extending into the aperture and configured to extend into the groove on a respective side of the shaft.

15. A seal assembly for sealing an opening in the wall of a blood vessel, the blood vessel having an interior wall surface, exterior wall surface, and a lumen, the seal assembly comprising:

a first sealing element for placing inside the lumen of the blood vessel;

a shaft having a rigid formation with the first sealing element and in a same predetermined configuration relative to the first sealing element before and after insertion of the first sealing element into the lumen, the shaft having a length sufficient to extend through the opening of the blood vessel and at least a portion of any overlying tissue;

an outer floating element slidingly movable along the shaft, the outer floating element having a top surface and a bottom surface; and a second sealing element, the second sealing element slidingly movable relative to the first sealing element along the shaft to engage the outer floating element and configured to position the bottom surface of the outer floating element against the exterior wall surface of the blood vessel to seal the opening in the blood vessel, wherein the shaft has at least two sides, the at least two sides each having a groove along a portion thereof and the outer floating element has an aperture to receive the shaft therethrough, the aperture having two protrusions extending into the aperture and configured to extend into the groove on a respective side of the shaft.

\* \* \* \* \*